United States Patent
Aliper et al.

(10) Patent No.: US 11,403,521 B2
(45) Date of Patent: Aug. 2, 2022

(54) MUTUAL INFORMATION ADVERSARIAL AUTOENCODER

(71) Applicant: Insilico Medicine, Inc., Rockville, MD (US)

(72) Inventors: Aleksandr Aliper, Moscow (RU); Aleksandrs Zavoronkovs, Rockville, MD (US); Alexander Zhebrak, Moscow (RU); Artur Kadurin, Taipei (TW); Daniil Polykovskiy, Moscow (RU); Rim Shayakhmetov, Moscow (RU)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 1038 days.

(21) Appl. No.: 16/015,990

(22) Filed: Jun. 22, 2018

(65) Prior Publication Data

US 2019/0392304 A1  Dec. 26, 2019

(51) Int. Cl.
  *G06N 3/08* (2006.01)
  *G10L 19/24* (2013.01)
  *G06N 7/00* (2006.01)
(52) U.S. Cl.
  CPC .............. *G06N 3/08* (2013.01); *G06N 3/088* (2013.01); *G06N 7/005* (2013.01); *G10L 19/24* (2013.01)
(58) Field of Classification Search
  CPC .......... G06N 3/08; G06N 3/088; G06N 7/005; G06N 3/0445; G06N 3/0472; G06N 3/0454; G10L 19/24; G16B 40/20
  (Continued)

(56) References Cited

U.S. PATENT DOCUMENTS

2015/0100530 A1   4/2015  Mnih et al.
2015/0213361 A1*  7/2015  Gamon ................. G06N 20/00
                                                                  706/12
(Continued)

FOREIGN PATENT DOCUMENTS

EP       3188111 A1      7/2017
WO       20180013247 A2  1/2018

OTHER PUBLICATIONS

Putin, Evgeny et al., "Adversarial Threshold Neural Computer for Molecular De Novo Design", Molecular Pharmaceutics, Dec. 15, 2017, Manuscript ID: mp-2017-01137w.
(Continued)

*Primary Examiner* — Don N Vo
(74) *Attorney, Agent, or Firm* — Maschoff Brennan; Jonathan M. Benns

(57) ABSTRACT

A method for generating an object includes: providing a dataset having object data and condition data; processing the object data to obtain latent object data and latent object-condition data; processing the condition data to obtain latent condition data and latent condition-object data; processing the latent object data and the latent object-condition data to obtain generated object data; processing the latent condition data and latent condition-object data to obtain generated condition data; comparing the latent object-condition data to the latent condition-object data to determine a difference; processing the latent object data and latent condition data and one of the latent object-condition data or latent condition-object data to obtain a discriminator value; and selecting a selected object based on the generated object data.

20 Claims, 11 Drawing Sheets

(58) Field of Classification Search
USPC .......................................................... 341/50
See application file for complete search history.

(56) References Cited

U.S. PATENT DOCUMENTS

| | | | |
|---|---|---|---|
| 2017/0228638 | A1 | 8/2017 | Danihelka et al. |
| 2017/0230675 | A1* | 8/2017 | Wierstra .............. G06N 3/0445 |
| 2018/0028294 | A1 | 2/2018 | Azernikov et al. |
| 2018/0039946 | A1* | 2/2018 | Bolte ................. G06Q 50/2057 |
| 2018/0082172 | A1* | 3/2018 | Patel ........................ G06N 3/08 |
| 2018/0174070 | A1* | 6/2018 | Hoffman ................. G06T 11/00 |

OTHER PUBLICATIONS

Kadurin A. et al.; "The cornucopia of meaningful leads: Applying deep adversarial autoencoders for new molecule development in oncology"; Oncotarget; Dec. 21, 2016; pp. 10883-10890, XP055471303; DOI: 10.18632/oncotarget.14073.

Aliper A. et al.; "Deep Learning Application for Predicting Pharmacological Properties of Druga and Drug Repurposing Using Transcriptomic Data"; Molecular Pharmeceutics, vol. 13, No. 7; Jul. 5, 2016; pp. 2524-2530; XP055800073; US ISSN: 1543-8384, DOI: 10.1021/acs.molpharmaceut/6b00248.

Artemov A.V. et al.; "Integrated Deep Learned Transcriptomic and Structure-based Predictor of Clinical Trials Outcomes"; bioRxiv; Dec. 29, 2016; XP055893302; DOI: 10.1101/095653; 21 pages.

Kadurin A. et al.; "druGAN: An Advanced Generative Adversarial Autoencoder Model for de Novo Generation of New Molecules with Desired Molecular Properties in Silico"; Molecular Pharmeceutics, vol. 14, No. 9; Sep. 5, 2017; pp. 3098-3104; XP055593031; US ISSN: 1543-8384, DOI: 10.1021/acs.molpharmaceut.7b00346.

Jing Y. et al.; "Deep Learning for Drug Design: an Artificial Intelligence Paradigm for Drug Discovery in the Big Data Era"; The AAPS Journal, Springer International Publishing, Cham, vol. 20, No. 3; Mar. 30, 2018 pp. 1-10; XP036534353; DOI: 10.1208/S12248-018-0210-0.

Chen H. et al.; "The rise of deep learning in drug discovery"; Drug Discovery Today, vol. 23, No. 6; Jan. 31, 2018; pp. 1241-1250; XP055664738; Amsterdam, NL ISSN: 1359-6446; DOI: 10.1016/j.drudis.2018.01.039.

European Patent Office; Extended European Search Report dated Feb. 28, 2022 issued in Application No. 19822510.4; 10 pages.

Ian Goodfellow, Jean Pouget-Abadie, Mehdi Mirza, Bing Xu, David Warde-Fariey, Sherjil Ozair, Aaron Courville, and Yoshua Bengio. Generative adversarial nets. In Z. Ghahramani, M. Welling, C. Cortes, N. D. Lawrence, and K. Q. Weinberger, editors, Advances in Neural Information Processing Systems 27, pp. 2672-2680, Curran Associates, Inc., 2014.

Antonia Creswell, Tom White, Vincent Dumoulin, Kai Arulkumaran, Biswa Sengupta, and Anil A. Bharath. Generative adversarial networks: An overview. CoRR, abs/1710.07035, 2017.

Mehdi Mirza and Simon Osindero. Conditional generative adversarial nets. CoRR, abs/1411.1784, 2014.

Alireza Makhzani, Jonathon Shlens, Navdeep Jaitly, and Ian J. Goodfellow. Adversarial autoencoders. CoRR, abs/1511.05644, 2015.

Guim Peramau, Joost van de Weijer, Bogdan Raducanu, and Jose M. Álvarez. Invertible conditional gansfor image editing. CoRR, abs/1611.06355, 2016.

Navaneeth Bodla, Gang Hua, and Rama Chellappa. Semi-supervised fusedgan for conditional image generation. CoRR, abs/1801.05551, 2018.

Zhifei Zhang, Yang Song, and Hairong Qi. Age progression/regression by conditional adversarial autoencoder. CoRR, abs/1702 08423,2017.

Grigory Antipov, Moez Baccouche, and Jean-Luc Dugelay. Face aging with conditional generative adversarial networks. CoRR, abs/1702.01983, 2017.

Guillaume Lample, Neil Zeghidour, Nicolas Usunier, Antoine Bordes, Ludovic DENOYER, and Marc Aurelio Ranzato. Fader networks:manipulating images by sliding attributes. In I. Guyon, U. V. Luxburg, S. Bengio, H. Wallach, R. Fergus, S. Vishwanathan, and R. Garnett, editors, Advances in Neural Information Processing Systems 30, pp. 5967-5976. Curran Associates, Inc., 2017. URL http://papers.nips.cc/paper/345 7178-fader-networksmanipulating-images-by-sliding-attributes.pdf.

Murat Kocaoglu, Christopher Snyder, Alexandros G. Dimakis, and Sriram Vishwanath. Causalgan: Learning causal implicit generative models with adversarial training. CoRR, abs/1709.02023, 2017.

Diederik P. Kingma and Max Welling. Auto-encoding variational bayes. CoRR, abs/1312.6114, 2013.

Kihyuk Sohn, Honglak Lee, and Xinchen Yan. Learning structured output representation using deep conditional generative models. In C. Cortes, N. D. Lawrence, D. D. Lee, M. Sugiyama, and R. Garnett, editors, Advances in Neura Information Processing Systems 28, pp. 3483-3491. Curran Associates, Inc., 2015.

Zhiting Hu, Zichao Yang, Ruslan Salakhutdinov, and Eric P. Xing. On unifying deep generative models. CoRR, abs/1706.00550,2017. URL http://arxiv.org/abs/1706.00550.

Jianmin Bao, Dong Chen, Fang Wen, Houqiang Li, and Gang Hua. CVAE-GAN: fine-grained image generation through asymmetric training. CoRR, abs/1703.10155, 2017.

Jun-Yan Zhu, Taesung Park, Phillip Isola, and Alexei A Efros. Unpaired image-to-image translation using cycle-consistent adversarial networks. arXiv preprint arXiv: 1703.10593, 2017.

Jiquan Ngiam, Aditya Khosla, Mingyu Kim, Juhan Nam, Honglak Lee, and Andrew Y. Ng. Multimodal deep learning. In Proceedings of the 28th International Conference on International Conference on Machine Learning, ICML'11, pp. 689-696, USA, 2011. Omnipress. ISBN 978-1-4503-0619-5. URL http://dl.acm.org/citation.cfm?id=3104482.3104569.

Weiran Wang, Raman Arora, Karen Livescu, and Jeff A. Bilmes. On deep multi-view representation learning Objectives and optimization. CoRR, abs/1602.01024, 2016. URL http://arxiv.org/abs/1602.01024.

WeiranWang, Honglak Lee, and Karen Livescu. Deep variational canonical correlation analysis. CoRR, abs/1610.03454, 2016. URL http://arxiv.org/abs/1610.03454.

Jimei Yang, Scott E. Reed, Ming-Hsuan Yang, and Honglak Lee. Weakly-supervised disentangling with recurrent transformations for 3d view synthesis CoRR, abs/1601.00706, 2016.

Attila Szabó, Qiyang Hu, Tiziano Portenier, Matthias Zwicker, and Paolo Favaro. Challenges in disentangling ndependent factors of variation. CoRR, abs/1711.02245, 2017.

Antonia Creswell, Anil A. Bharath, and Biswa Sengupta. Conditional autoencoders with adversarial information Factorization. CoRR, abs/1711.05175, 2017.

Shengjia Zhao, Jiaming Song, and Stefano Ermon. Infovae: Information maximizing variational autoencoders. CoRR, abs/1706.02262, 2017.

Yang Li, Quan Pan, Suhang Wang, Haiyun Peng, Tao Yang, and Erik Cambria. Disentangled variational auto-encoder for semi-supervised learning CoRR, abs/1709.05047, 2017.

Xi Chen, Yan Duan, Rein Houthooft, John Schulman, Ilya Sutskever, and Pieter Abbeel. Infogan: Interpretable representation learning by information maximizing generative adversarial nets CoRR, abs/1606.03657, 2016.

Qiyang Hu, Attila Szabo, Tiziano Portenier, Matthias Zwicker, and Paolo Favaro. Disentangling factors of variation by mixing them CoRR, abs/1711.07410, 2017.

Marwin H. S. Segler, Thierry Kogej, Christian Tyrchan, and Mark P.Waller. Generating focused molecule libraries for drug discovery with recurrent neural networks. ACS Central Science, 4 (1):120-131, Dec. 2017.

Artur Kadurin, Sergey Nikolenko, Kuzma Khrabrov, Alex Aliper, and Alex Zhavoronkov. druGAN: An advanced generative adversarial autoencoder model for de novo generation of new molecules with desired molecular properties in silico. Molecular Pharmaceutics, 14(9): 3098-3104, Aug. 2017.

Rafael Gómez-Bombarelli, David K. Duvenaud, JoséMiguel Hernandez-Lobato, Jorge Aguilera-lparraguirre, Timothy D. Hirzel, Ryan P.

(56) References Cited

OTHER PUBLICATIONS

Adams, and Alán Aspuru-Guzik. Automatic chemical design using a data-driven continuous Yepresentation of molecules. CoRR, abs/1610.02415, 2016.

Mihaela Rosea, Balaji Lakshminarayanan, David Warde-Fariey, and Shakir Mohamed. Variational approaches for auto-encoding generative adversarial networks. CoRR, abs/1706.04987, 2017.

Florian Schroff, Dmitry Kalenichenko, and James Philbin. Facenet: A unified embedding for face recognition and clustering. CoRR, abs/1503.03832, 2015.

Weiran Wang, Raman Arora, Karen Livescu, and Jeff Bilmes. On deep multi-view representation learning. In Proceedings of the 32nd International Conference on International Conference on Machine Learning—vol. 37, ICML'15, pp. 1083-1092. JMLR.org, 2015. URL http://dl.acm.org/citation.cfm?id=3045118.3045234.

Mohamed Ishmael Diwan Belghazi, Sai Rajeswar, Aristide Baratin, Devon R Hjelm, and Aaron Courville. Mine: Mutual Information neural estimation. arXiv e-prints, 1801.04062, Jan. 2018. URL https://arxiv.org/abs/1801.04062.

Qiaonan Duan, Corey Flynn, Mario Niepel, Marc Hafner, Jeremy L. Muhlich, Nicolas F. Fernandez, Andrew D. Rouillard, Christopher M. Tan, Edward Y. Chen, Todd R. Golub, Peter K. Sorger, Aravind Subramanian, and Avi Ma'ayan. LINCS canvas browser: interactive web app to query, browse and interrogate LINCS l1000 gene expression signatures. Nucleic Acids Research, 42(W1):W449-W460, Jun. 2014.

Kumar Sricharan, Raja Bala, Matthew Shreve, Hui Ding, Kumar Saketh, and Jin Sun. Semi-supervised conditional gans. CoRR, abs/1708.05789, 2017.

David S. Wishart, Craig Knox, Anchi Guo, Dean Cheng, Savita Shrivastava, Dan Tzur, Bijaya Gautam, and Murtaza Hassanali. Drugbank: a knowledgebase for drugs, drug actions and drug targets. Nucleic Acids Research, 36 (Database-Issue):901-906, 2008.

United States Patent and Trademark Office; International Search Report and Written Opinion dated Aug. 19, 2019, issued in Int'l Application. No. PCT/US2019/033960, 7 pages.

\* cited by examiner

MUTUAL INFORMATION ADVERSARIAL AUTOENCODER

BACKGROUND

Deep neural networks (DNNs) are computer system architectures that have recently been created for complex data processing and artificial intelligence (AI). DNNs are machine learning models that employ more than one hidden layer of nonlinear computational units to predict outputs for a set of received inputs. DNNs can be provided in various configurations for various purposes, and continue to be developed to improve performance and predictive ability.

The background architectures can include generative adversarial networks (GANs), which are involved in deep learning to generate novel objects that are indistinguishable from data objects. Conditional GANs or supervised GANs generate objects matching a specific condition.

It would be advantageous to have a computer method for generating an object that satisfies a condition using one or more DNNs, which may include conditional GANs or supervised GANs.

SUMMARY

In some embodiments, a method for generating an object can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent condition-object data to determine a difference; processing the latent object data and latent condition data and one of the latent object-condition data or latent condition-object data with a discriminator to obtain a discriminator value; obtaining better latent object data, latent object-condition data or latent condition-object data, and/or latent condition data based on the discriminator value, difference between object-condition data and condition-object data, and difference between object with generated object and condition with generated condition; obtaining an object (e.g., selecting a selected object) based on the generated latent object data and latent condition-object data from a given condition; obtaining a physical form of the selected object; and validating the physical form of the selected object.

In some embodiment, the method can include selecting a selected object from the generated object data based on the difference between latent object-condition data of generated object with latent condition-object data; obtaining a physical form of the selected object; and validating the physical form of the selected object.

In some embodiments, a computer program product can include a non-transient, tangible memory device having computer-executable instructions that when executed by a processor, cause performance of a method that can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent-condition data to determine a difference; processing the latent object data and latent condition data and one of the latent object-condition data or latent condition-object data with a discriminator to obtain a discriminator value; changing latent object data, latent object-condition data or latent condition-object data, and/or latent condition data based on the discriminator value and difference between object-condition data and condition-object data; obtaining a selected object based on the generated object data, and latent generated condition-object data from given condition; and providing the selected object in a report with a recommendation for validation of a physical form of the object.

In some embodiment, the method performed by the computer program product can include selecting a selected object from the generated object data based on the difference between latent object-condition data of generated object with latent condition-object data; obtaining a physical form of the selected object; and validating the physical form of the selected object.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1A:
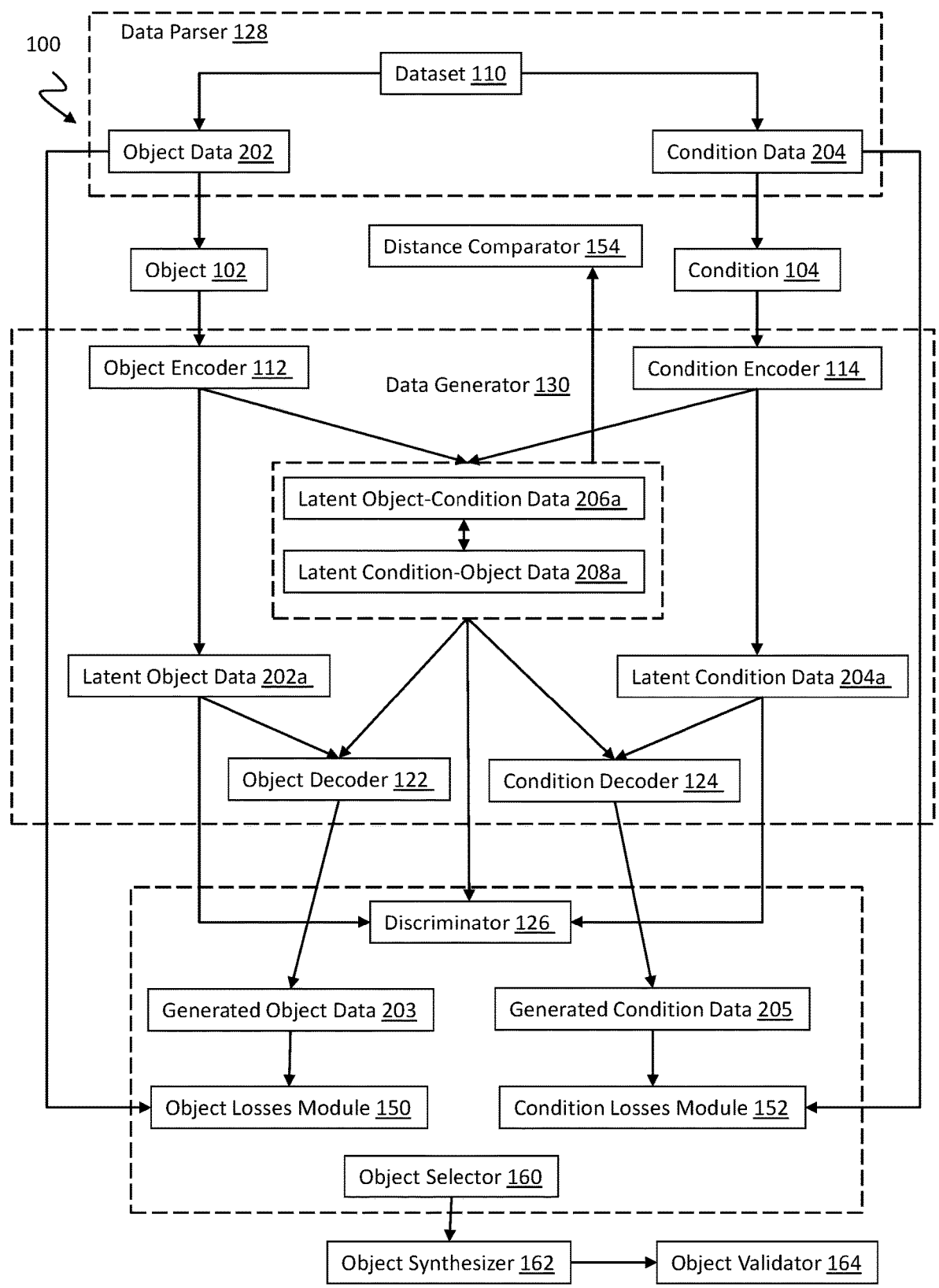
FIG. 1A illustrates an embodiment of a Mutual Information Adversarial Autoencoder (MIAAE).

The elements of the figures are arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

An autoencoder (AE) is a type of deep neural network (DNN) used in unsupervised learning for efficient information coding. The purpose of an AE is to learn a representation (e.g., encoding) of objects. An AE contains an encoder part, which is a DNN that transforms the input information from the input layer to the latent representation, and includes a decoder part, which decodes an original object with the output layer having the same dimensionality as the input for the encoder. Often, a use of an AE is for learning a representation or encoding for a set of data. An AE learns to compress data from the input layer into a short code, and then uncompress that code into something that closely matches the original data. In one example, the original data may be a molecule that interacts with a target protein, and thereby the AE can design a molecule that is not part of an original set of molecules or select a molecule from the original set of molecules or variation or derivative thereof that interacts (e.g., binds with a binding site) of the target protein.

Generative Adversarial Networks (GANs) are structured probabilistic models that can be used to generate data. GANs can be used to generate data (e.g., a molecule) similar to the dataset (e.g., molecular library) GANs are trained on. A GAN can include two separate modules, which are DNN architectures called: (1) discriminator and (2) generator. The discriminator estimates the probability that a generated product comes from the real dataset, by working to compare a generated product to an original example, and is optimized to distinguish a generated product from the original example. The generator outputs generated products based on the original examples. The generator is trained to generate products that are as real as possible compared to an original example. The generator tries to improve its output in the form of a generated product until the discriminator is unable to distinguish the generated product from the real original example. In one example, an original example can be a molecule of a molecular library of molecules that bind with a protein, and the generated product is a molecule that also can bind with the protein, whether the generated product is a variation of a molecule in the molecular library or a combination of molecules thereof or derivatives thereof.

Adversarial AutoEncoders (AAEs) are probabilistic AEs that use GANs to perform variational inference. AAEs are DNN-based architectures in which latent representations are forced to follow some prior distribution via the discriminator.

Conditional GANs, also referred to as supervised GANS, include specific sets of GAN-based architecture configured for generating objects that match a specific condition. In the usual conditional GAN training process, both the generator and discriminator are conditioned on the same external information (e.g., object and condition pair, such as molecular and target protein pair that bind), which are used during generation of a product.

In one embodiment, the imposed condition of a conditional GAN is fulfilled by the generated object (e.g., product) being as complex as the object itself. The DNN architecture can be used for the generation of specific molecules (e.g., generated object or product) having a desired action on human cells (e.g., condition), or one or more molecules (e.g., generated object or product) that bind to a target protein (e.g., condition). Those problems are common in the field of drug discovery. In both cases, the condition (a protein, or a cell state before receiving a molecule and a cell state after receiving the molecule) is at least as complex as the object (a candidate molecule for a drug) itself.

FIG. 1A shows a DNN's architecture 100 that can perform the methods described herein. As shown, a dataset 110 is provided. For example, the dataset 110 can include object data 202 (e.g., molecule, molecular structure) and condition data 204 (e.g., cell state before interacting with molecule and cell state after interacting with molecule). The object data 202 is identified for the object 102 and the condition data 204 is identified for the condition 104. The object data 202 is input into an object encoder 112, which generates the latent object data 202*a* and latent object-condition data 206*a*. The condition data 202 is input into a condition encoder 114, which generates the latent condition data 204*a* and the latent condition-object data 208*a*. Optionally, the latent object-condition data 206*a* can be compared to the latent condition-object data 208*a* to make sure they are the same or substantially the same within some tolerance threshold. The tolerance threshold can be defined. Often, the latent object-condition data 206*a* is nearly identical to the latent condition-object data 208*a*, and thereby both may be referred to generally as the object-condition data 206*a*.

In an example, the dataset 110 is provided with three parts, which can be distinct from each other such as in rows, columns, or other association. This allows a first entry in the first part to be associated with a first entry in the second part and a first entry in the third part. This ties the first entry in each part together. The first entry of the first part can be a molecule, the first entry of the second part is a cell state prior (e.g., prior cell state) to the cell interacting with the molecule, and the first entry of the third part is a cell state subsequent (e.g., subsequent cell state) to interacting with the molecule. Accordingly, the entries of the first part are provided to the object encoder 112 and the entries of the second part and entries of the third part are provided to the condition encoder 114. It should be recognized that the object data 202 and condition data 204 may take other forms, such as a molecule as the object and a protein as the condition, where the object binds with the protein.

In one option, a data parser 128 can be programed to parse the dataset 110 into the object data 202 (e.g., by selecting the first part, such as a first column) and into the condition data 204 (e.g., selecting the second and third parts, such as the second and third columns).

In some embodiments, the object encoder 112 operates separately from the condition encoder 114, and vice versa.

This allows both encoders to operate independently of one another; however, they both produce the latent object-condition data 206a and condition-object data 208a, which ideally are the same. In an ideal model, the vector of the object-condition data 206a and vector of the condition-object data 208a are the same.

As shown in FIG. 1A, the latent object data 202a and latent object-condition data 206a are input into an object decoder 122, and the latent condition data 204a and latent condition-object data 208a (e.g., same as the latent object-condition data 206a) are input into a condition decoder 124. The object decoder 122 produces generated object data 203, and the condition decoder 124 produces generated condition data 205. The generated object data 203 is processed through an object losses module 150 with the object data 202, and the losses are computed to determine how well the data generator 130 (e.g., molecule generator model) performed. Less losses indicate higher data generator 130 performance that produces generated object data 203 that is close to the object data 202. An object data loss threshold can be defined, and the object data loss must be within the predetermined object data loss threshold in order for the data generator 130 to be determined to be sufficiently operational.

Similarly, the generated condition data 205 is processed through a condition losses module 152 with the condition data 204, and the losses are computed to determine how well the data generator 130 (e.g., condition generator model) performed. Less losses indicate higher data generator 130 performance that produces generated condition data 205 that is close to the condition data 204. A condition data loss threshold can be defined, and the condition data loss must be within the predetermined condition data loss threshold in order for the data generator 130 to be determined to be sufficiently operational.

In some embodiments, the latent object-condition data 206a is compared with the latent condition-object data 208a with a distance comparator 154 in order to determine the distance from each other. The distance is also used to determine how well the data generator 130 is performing.

The distance data from the distance comparator 154, along with the object data loss from the object losses module 150 and condition data loss from the condition losses module 152, may be analyzed with regard to relative thresholds to determine if the data generator 130 is operating within acceptable bounds.

In the example where the object 102 is a molecule and the condition 104 is the prior cell state and subsequent cell state for the cell in relation to exposure to the molecule, the generated object data 203 can be a molecular structure or molecular library thereof. Similarly, the generated condition data 205 can be a prior cell state and a subsequent cell state for that molecule, or a data library thereof. An example of the generated condition data 205 can be transcriptome data prior and subsequent to exposure to the molecule (or molecular library of generated object data 203).

In some embodiments, the object 102 includes distributions of molecular structures, and the condition 104 includes distributions of the prior cell states and subsequent cell states. The goal of the data generator 130 is to generate one or more molecules in the generated object data 203 so as to provide generated object data molecules or molecule distributions that fit within the distributions of molecular structures of the object 102. Another goal of the data generator 130 is to generate one or more conditions in the generated condition data 205 so as to provide generated condition data distributions that fit within the distributions of prior cell state and subsequent cell state of the condition 104.

Additionally, the discriminator 126 of FIG. 1A can be configured to receive as input the latent object data 202a, latent object-condition data 206a (and/or condition-object data 208a), and latent condition data 204a. The discriminator 126 computes a single number that provides an indication as to how close the generated object data distributions are to the object 102 and/or how close the generated condition data distributions are to the condition 104. The discriminator 126 can pull the latent object data 202a, latent object-condition data 206a (and/or condition-object data 208a), and latent condition data 204a together and compare the same to the distribution of the object data 202 and/or condition data 204. The comparison can be against a standard normal distribution for the data in the object data 202 and/or condition data 204. The MIAAE model includes the discriminator 126 for $N(0,I)$ versus $<z_x, z_{yx}, z_y>$ and/or $<z_x, z_{xy}, z_y>$.

In an example, the output of the object encoder 112 and output of the condition encoder 114 are analyzed for a specific distribution. For example, the distribution of the object information (e.g., latent object data 202a) should be a standard normal distribution. For example, all the molecules (e.g., object data 202) are processed through the object encoder 112 to get the latent object data 202a, which includes generated molecules that are distributed as a standard deviation distribution. The discriminator 126 performs the data processing in order to determine if the generated molecules (e.g., latent object data 202a) are within a standard deviation distribution of the object data 202. This is also done for the latent condition data 204a. Optionally, this can be done for the latent object-condition data 206a and latent condition-object data 208a. These three vectors (e.g., latent object data 202a, latent condition data 204a, and latent object-condition data 206a) are determined to be independent in the sense that the joint information that is contained in both the object 102 and the condition 104, should be independent from and separate information that relates only to the object 102 that is object specific, and relates only to the condition 104 that is condition specific. This is also ensured by the discriminator 126. The discriminator 126 compares the latent distributions from the object encoder 112 and condition encoder 114 with samples from the distributions (e.g., standard distribution) of the object 102 and the condition 104.

In some embodiment, the molecules of the generated object data 203 are analyzed, and one or more specific molecules that fit the condition criteria are selected. The selected one or more molecules are then selected and synthesized before being tested with one or more cells to determine whether or not the synthesized molecules actually satisfy the condition 104.

In some embodiments, the architecture 100 is a computer model that can be implemented in a computer or computing system. The model is configured to generate a molecule with a proper transcription response in accordance with the prior cell state and subsequent cell state. Once one or more molecules are generated along with transcription data, the model can categorize the molecules according to whatever profile is desirable. A specific prior cell state and subsequent cell state can be prioritized, and then a molecule with a profile that matches the profile the prior cell state and subsequent cell state is selected and synthesized. As such, an object selector 160 (e.g., molecule selector), which can be a software module, selects at least one molecule for synthesis. The selected molecule is then provided to an object synthesizer 162. The dashed line boxed around the discriminator 126, generated object data 203, generated condition data

205, object losses module 150 and condition losses module 152 can be utilized for facilitating operation of the object selector 160. The selected object (e.g., molecule) is then provided to the object synthesizer 162 (e.g., molecule synthesizer), where the selected object (e.g., selected molecule) is then synthesized. The synthesized object (e.g., molecule) is then provided to the object validator 164 (e.g., molecule validator, which tests the object to see if it satisfies the condition 104. For example, a synthesized object that is a molecule can be tested with live cell cultures or other validation techniques in order to validate that the synthesized molecule satisfies the condition 104.

Figure 2A:
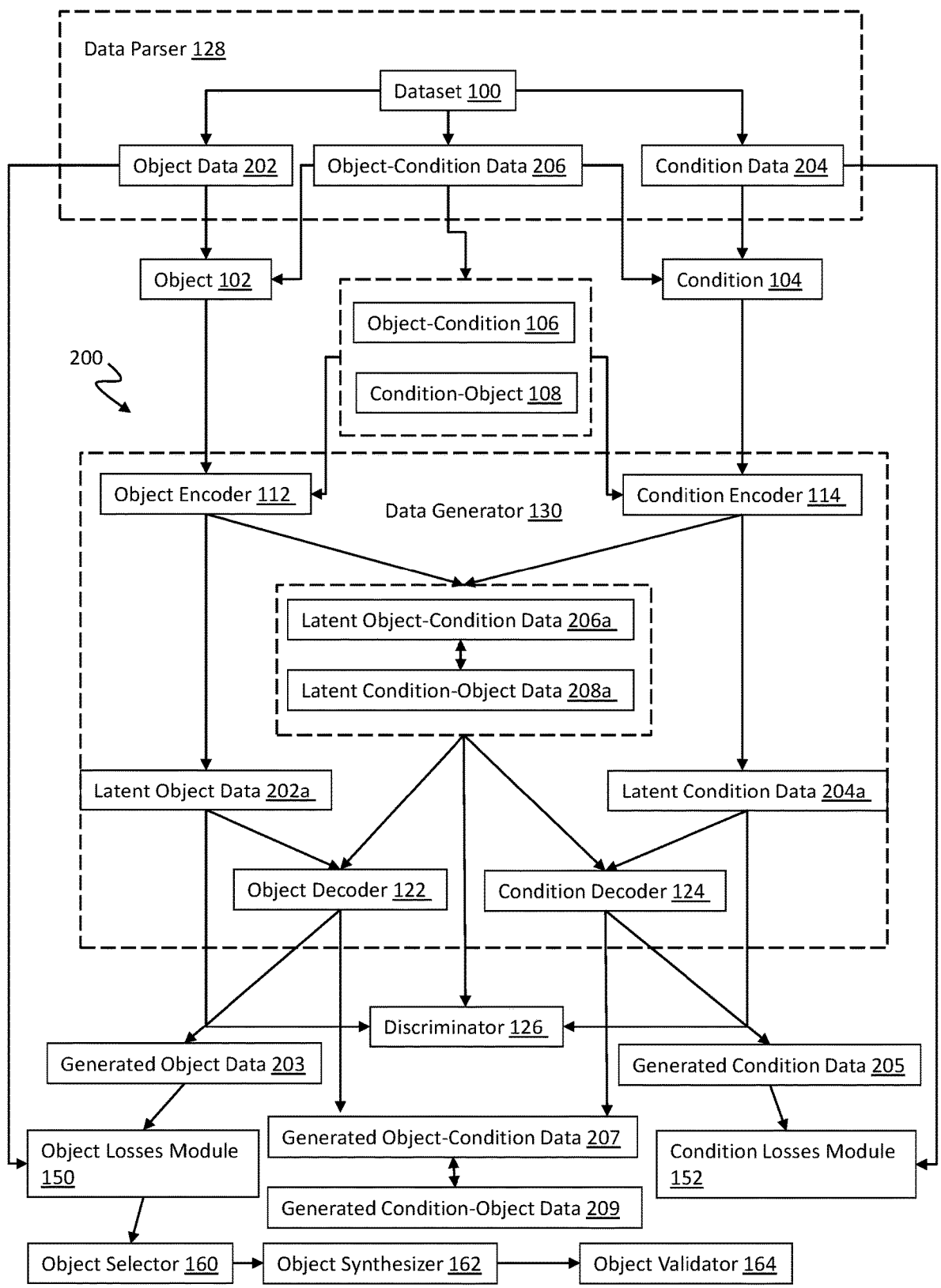
FIG. 2A illustrates an embodiment of a MIAAE.

In accordance with FIG. 1A, a design method 170 can include providing a dataset 110 having object data 202 for the object 102 (object data 202) and the condition data 204 for the condition 104 (condition data 204) (Step 172). Optionally, the dataset 110 can include object-condition data 206a and/or condition-object data 208a for a combination of the object and the condition 106 (object-condition data 206a and/or condition-object data 208a) as shown in FIG. 2A.

The method 170 can include processing object data 202 of the dataset 110 to obtain latent object data 202a and latent object-condition data 206a with an object encoder 112 (Step 174). Additionally, the method 170 can include processing condition data 204 of the dataset 110 to obtain latent condition data 204a and latent condition-object data 208a with a condition encoder 114 (Step 176).

The method 170 can include processing the latent object data 202a and latent object-condition data 206a to obtain generated object data 203 with an object decoder 122 (Step 178). Additionally, the method 170 can include processing the latent condition data 204a and latent condition-object data 208a to obtain generated condition data 205 with a condition decoder 124 (Step 180).

The method can include comparing the generated object data 203 with the object data 202 with an object losses module 150 (Step 182). During such a comparison, losses from the object data 202 to the generated object data 203 can be calculated (Step 182a). The calculated losses can be compared to a losses threshold (Step 182b). Then, a generated object of the generated object data 203 can be selected such as with an object selector 160 (Step 184), wherein the selected object is a generated object that is less than the threshold. This can include selecting a selected generated object data that is less than a threshold object difference between the generated object data 203 and the object data 202 (Step 184).

In some embodiments, the method can include comparing the generated condition data 205 with the condition data 204 with a condition losses module 152 (Step 186). During such a comparison, losses from the condition data 204 to the generated condition data 205 can be calculated (Step 186a). The calculated losses can be compared to a losses threshold (Step 186b). Then, a generated condition of the generated condition data 205 can be selected such as with a condition selector (Step 188), wherein the selected condition is a generated condition that is less than the threshold. This can include selecting a selected generated condition data that is less than a threshold condition difference between the generated condition data 205 and the condition data 204 (Step 188).

When the selected generated condition is selected, then the corresponding generated object is identified and selected (Step 190).

Once a generated object is selected (Step 184 and/or Step 190, then the method 170 includes validating the selected object (Step 192). The validation can be performed as described herein. When the object is a molecule, the validation can include synthesis and then testing with live cells.

FIG. 2A shows a DNN's architecture 200 that can perform the methods described herein. The DNN's architecture 200 can include a data parser 128, which can be configured to parse the data of a dataset 110 that can be separated into object data 202 (e.g., only object data), condition data 204 (e.g., only condition data), and object-condition data 206. The object 102 can be defined by the object data 202 and object-condition data 206. The condition can be defined by the condition data 204 and the object-condition data 206. The object-condition data 206 may be defined to be an object-condition 106 or a condition-object 108, which may include only the object-condition data 206 or a combination of the object data 202 and object-condition data 206 or a combination of the condition data 204 and object-condition data 206. The object-condition 106 can be substantially the same as the condition-object 108.

The DNN's architecture 200 can also include a data generator 130 that includes an object encoder 112 that is configured to generate latent object data 202a and latent object-condition data 206a. The data generator 130 can also include a condition encoder 114 that is configured to generate latent condition data 204a and latent condition-object data 208a. The latent object-condition data 206a can be the same or about the same within a tolerance or a defined difference threshold as the condition-object data 208a, where the difference therebetween may merely be which encoder (e.g., object encoder 112 or condition encoder 114) performs the calculations and modeling.

The object encoder 112 and/or condition encoder 114 can be configured as an autoencoder (AE), and can learn a representation of an object 102 or condition 104 and transform the data to the latent representations.

The data generator 130 also can include an object decoder 122 that generates generated object data 203 and a condition decoder 124 that generates generated condition data 205. In some instances, the object decoder 122 and/or condition decoder 124 can generate generated object-condition data 207 and/or generated condition-object data 209.

The object decoder 122 and/or condition decoder 124 can be configured to process the latent representations in order to generate the generated data (e.g., generated object data 203, generated condition data 205, etc.). The generated data can be as close to the data of the dataset 110 as possible.

The DNN's architecture 200 can also include a discriminator 126 that can be configured to analyze the generated object data 203 and/or generated condition data 205. Optionally, the discriminator 126 can be configured to analyze the generated object-condition data 207 and/or generated condition-object data 209. The discriminator 126 can be configured (e.g., programmed) to perform various analyses, such as: comparing generated object data 203 with object data 202; comparing generated condition data 205 with condition data 204; or comparing generated object-condition data 207 or generated condition-object data 209 with object-condition data 206. The discriminator 126 may be configured to estimate the probability that the generated data (e.g., generated object data 203, generated condition data 205, generated object-condition data 207 or generated condition-object data 209) is the same as or within a standard deviation of the source data of the dataset 110, whether parsed or non-parsed.

Figure 6:
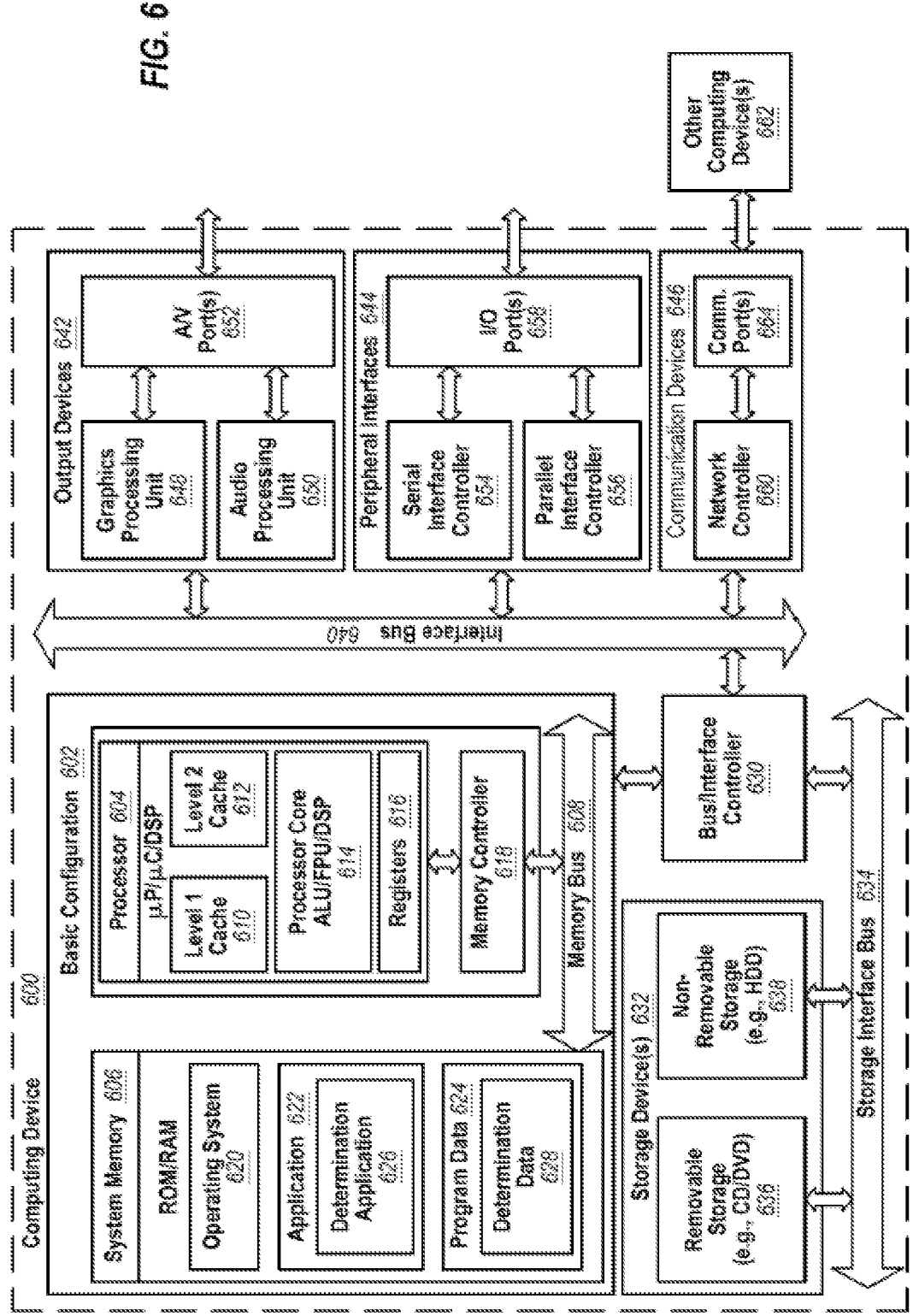
FIG. 6 illustrates an embodiment of a computing device.

It should be recognized that the data parser 128, data generator 130 and discriminator 126 can be configured as a computing system or individual computers, such as shown in FIG. 6. As such, each can be a unique computer, combined into a computer, or distributed across a computer network, such as a cloud computer network. Thus, each can include the components of a computer.

Also, aspects of FIG. 1A are included in FIG. 2A, which can operate as described herein, such as the objects losses module 150, condition losses module 152, object selector 160, object synthesizer 162, and object validator 164.

The DNN's architecture 200 can be used in the methods described herein.

Figure 2B:
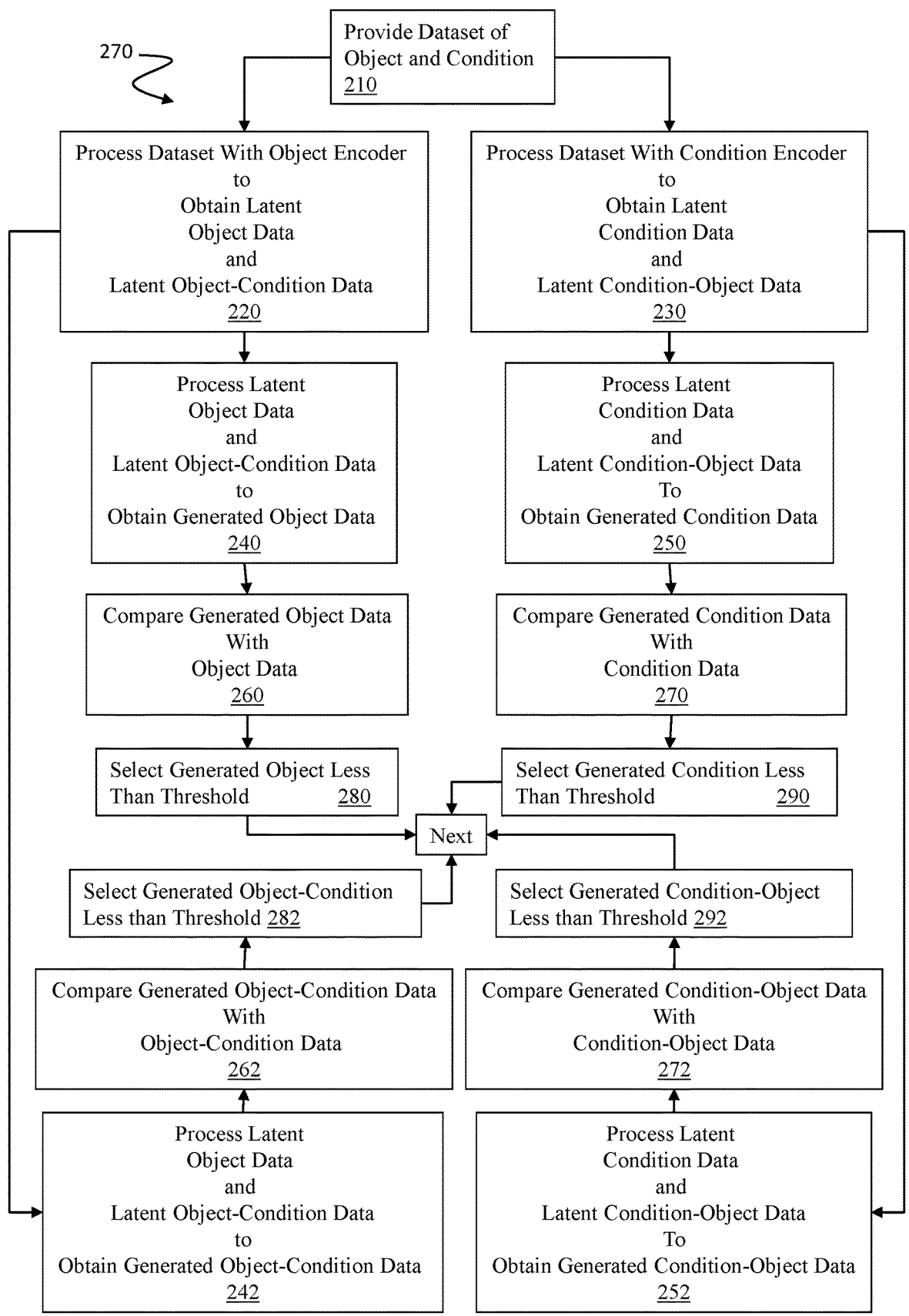
FIG. 2B illustrates an embodiment of a method for operation of the MIAAE of FIG. 2A.

FIG. 2B shows an example of a design method 270 for designing an output object 102 and an output condition 104, which can be similar within a distribution to the input object 102 and input condition 104. As such, the output object 102 may be substantially similar to the input object 102 or distribution thereof and the output condition 104 may be substantially similar to the input condition 104. The purpose can be for the output to function for the conditions of the input.

Figure 3:
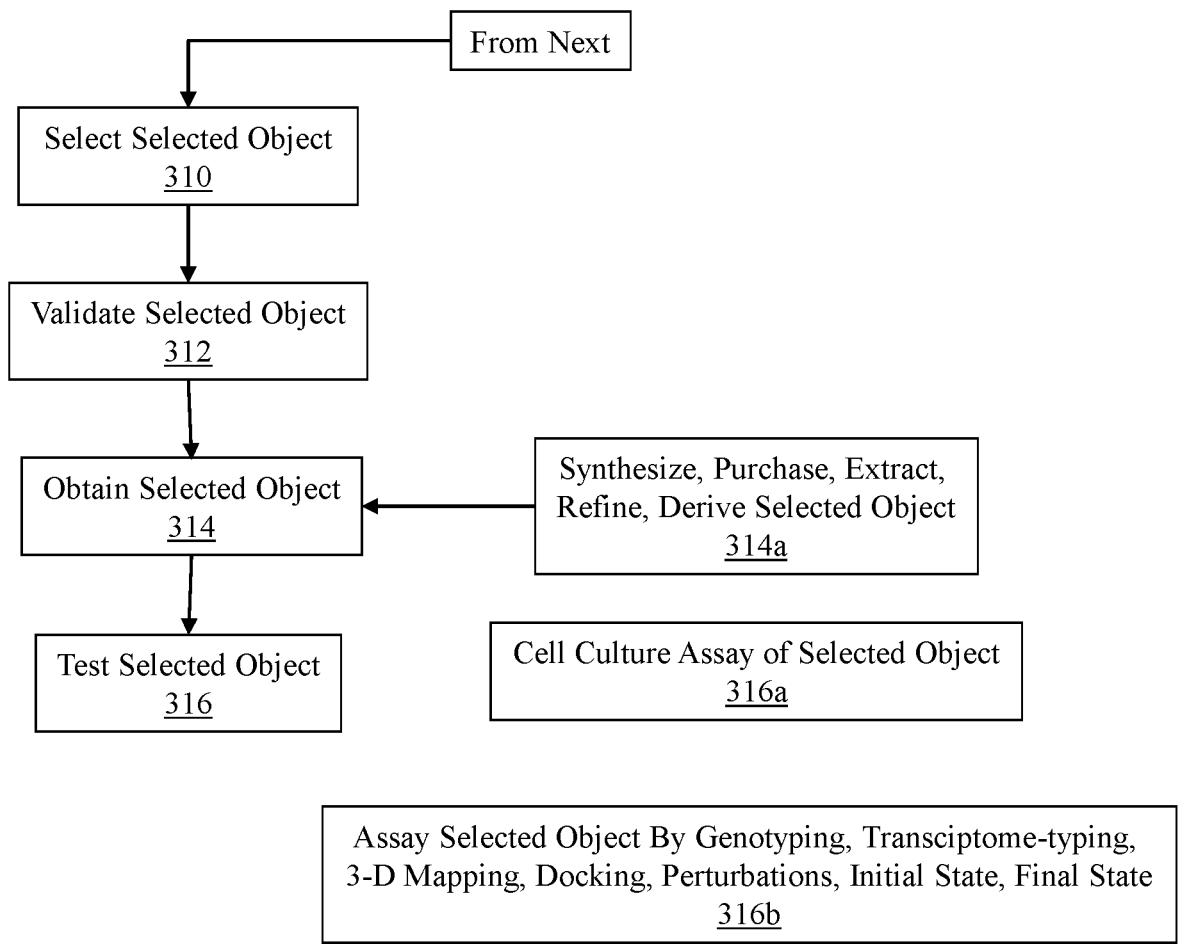
FIG. 3 illustrates an embodiment of a method for operations upon selecting a selected object for further processing.

The design method 270 can include: providing a dataset 110 having object data 202 for the object 102 (object data 202), condition data 204 for the condition 104 (condition data 204), and object-condition data 206 and/or condition-object data 208 for a combination of the object and the condition 106 (object-condition data 206 and/or condition-object data 206) (Step 210); processing data of the dataset 110 to obtain latent object data 202a and latent object-condition data 206a with an object encoder 112 (Step 220); processing data of the dataset 110 to obtain latent condition data 204a and latent condition-object data 208a with a condition encoder 114 (Step 230); processing the latent object data 202a and latent object-condition data 206a to obtain generated object data 203 with an object decoder 122 (Step 240); processing the latent condition data 204a and latent condition-object data 208a to obtain generated condition data 205 with a condition decoder 122 (Step 250); performing at least one of: comparing the generated object data 203 with the object data 202 (Step 260); and selecting a selected generated object data 203 that is less than a threshold object difference between the generated object data 203 and the object data 202 (Step 280); or comparing the generated condition data 205 with the condition data 204 (Step 270); and selecting a selected generated condition data 205 that is less than a threshold condition difference between the generated condition data 205 and the condition data 204 (Step 290); selecting a selected object 203 that corresponds with the selected generated object data or that corresponds with the selected generated condition data 205 (Step 310); and validating the selected object (Step 312) as shown in FIG. 3.

In some embodiments, the method 270 may optionally include processing the latent object data 202a and latent object-condition data 206a to obtain generated object-condition data 207 with an object decoder 122 (Step 242); and processing the latent condition data 204a and latent condition-object data 208a to obtain generated condition-object data 209 with a condition decoder 124 (Step 252). The method 270 may include performing at least one of: comparing the generated object-condition data 207 with the object-condition data 206 (Step 262); and selecting a selected generated object-condition data that is less than a threshold object-condition difference between the generated object-condition data 207 and the object-condition data 206 (Step 282); or comparing the generated condition-object data 209 with the condition-object data 208 (Step 272); and selecting a selected generated condition-object data that is less than a threshold condition-object difference between the generated condition-object data 209 and the condition-object data 208 (Step 292). Then, the method 270 includes selecting a selected object 203b that corresponds with the selected generated object-condition data 207a or that corresponds with the selected generated condition-object data 209a (Step 310); and validating the selected object 203b (Step 312) as shown in FIG. 3.

In some embodiments, the methods, such as 170 or 270 or other, may include: obtaining a physical object for the selected object 203 (Step 314); and testing the physical object with the condition 104 (Step 316), as shown in FIG. 3. Also, in any method the obtaining of the physical object can include at least one of synthesizing, purchasing, extracting, refining, deriving, or otherwise obtaining the physical object (Step 314a). The physical object may be a molecule or other. The methods may include the testing involving assaying the physical object in a cell culture (Step 316a). The methods may also include assaying the physical object by genotyping, transcriptome-typing, 3-D mapping, ligand-receptor docking, before and after perturbations, initial state analysis, final state analysis, or combinations thereof (Step 316b). Preparing the physical object for the selected generated object 203 can often include synthesis when the physical object is a new molecular entity. Accordingly, the methods may include selecting a generated object that is not part of the dataset 110 or object data 202.

In some embodiments, an initial dataset can be used as an input for the system described herein (e.g., FIGS. 1A, 2B, etc.). The dataset can include a transcriptome dataset from the LINCS L1000 project. This dataset contains information about the cell states before (e.g., prior cell state) and after (e.g., subsequent cell state) addition of a molecule at a specific dosage. Within the dataset, each cell state can be represented by a set of gene expression profiles. The gene expression profiles are genomic measurements, which show whether or not a gene is present within the cell at the time of measurement (e.g., prior cell state or subsequent cell state). These gene expression profiles can contain from hundreds to thousands genes. Within the LINCS L1000 project, there are various datasets corresponding to the case of different molecules applied to different types of cells. In each case for a molecule, the dataset gives information about the effect that molecule had on the overall cell state (e.g., prior cell state, transitioning cell state, and subsequent cell state).

For each cell line, the training dataset contains replicated experiments. Each of the conditions in the training dataset is characterized by the label of the molecule, the molar concentration of the molecule, the cell state before addition of the molecule and the cell state after the molecule has been added and cell state has undergone perturbations. This data can be used to train the object encoder 112 and condition encoder 114.

The system uses two types of inputs. A first input is the molecule (e.g., the object) and second input is the transcriptomic measurements of the cell states before (e.g., prior cell state) and after (e.g., subsequent cell state) the molecule is added to the cell (e.g., the condition). The data are organized as a set of molecule-condition pairs, in which the condition includes a specific dose of the molecule and the prior cell state and subsequent cell state after reacting to the molecule. In order to extract the relevant features, a specific encoder architecture was designed, such as object encoder 112 and condition encoder 114.

When the DNN-based methods described herein are used for tasks, such as new molecule design and molecular feature extraction, drug-like molecular structure can be represented using a string, such as in formats like SMILES (simplified molecular-input line-entry system).

The architecture design presented herein, such as in FIGS. 1A and 2A can be called "Mutual Information Adversarial Autoencoder" (MIAAE), which is an improved conditional AAE system that specifically addresses the case when the condition is a complex object and the condition contains irrelevant information. Specifically, MIAAE extracts have shared information between the condition and the object as well as their mutually independent information. This extracted information can be used to generate new molecules that can function to satisfy the condition.

The MIAAE explicitly decouples shared information in the dataset by forcing the model of the architecture (e.g., 100 or 200) to split the latent representations of the object and the condition that are created by the object encoder 112 and condition encoder 114 into three parts: a common part (e.g., latent object-condition data 206a), and two separate parts (e.g., latent object data 202a and latent condition data 204a), wherein all three parts are mutually independent. As MIAAE learns to extract various kinds of information properly, it is able to decouple useless and useful information for conditional generation.

The MIAAE is designed as a novel system that aims at being applied to general problems involving conditional generation of a complex object (e.g., molecule) given a specified complex condition (e.g., cell states before and after exposure to the molecule). Information about the object and condition are provided as datasets of pairs (e.g., Object, Condition). A specific feature of the architecture 100, 200 is the ability to handle problems in which both the object and the condition are assumed to have a certain level of complexity, as in the case of molecules and altered cell states in response to the molecule.

As shown in the figures, the data generator 130 of the model (e.g., architecture 100, 200) is made of two pairs of encoder-decoder. A first encoder being the object encoder 112 produces the latent representation of the object (e.g., latent object data 202a and latent object-condition data 206a). The latent representation of the object is split into two parts: (1) latent object data 202a being a first part corresponding to information specific to the object alone (e.g., different variations of molecules with the same binding properties) which excludes all information about the condition; and (2) latent object-condition data 206a being a second part corresponding to common information between the object and the condition. The latent object-condition data 206a contains shared information about which molecules can bind to which binding site of a protein, such as in order to affect a change in cell state. A separate second encoder being the condition encoder 114 performs the same types of tasks, but for generating the latent representation of the condition (e.g., latent condition data 204a and latent condition-object data 208a). The information for the latent representation of the condition is also split in two parts: (1) latent condition data 204a is a first part that corresponds to the information specific to the condition alone (e.g., all information about the protein except its binding site); and (2) latent condition-object data 208a that is a second part that contains shared information between the condition and the object. Optimally, the latent object-condition data 206a is identical to the latent condition-object data 208a, or within a difference threshold. These encoders can generate the latent representations for the object and the condition. This leads to 3 types of variables: variable 1 corresponding to information specific to "x", wherein it should contain all information about the protein except its binding site; variable 2 corresponding to information specific to "y", wherein it represents information about different variations of molecules with the same binding properties; and variable 3 corresponding to information common between "x" and "y", wherein it contains common information about which molecules can bind to which binding site of a protein.

The decoders, such as the object decoder 122 and condition decoder 124 use the latent representations produced by the object encoder 112 and condition encoder 114. The object decoder 122 attempts to reconstruct the original object 102 using the latent representation of the object (latent object data 202a) given the condition 104, whereas the condition decoder 124 performs a similar task using the latent representation of the condition (latent condition data 204a) provided by the condition encoder 114.

Another part of the model is the discriminator 126. This discriminator 126 serves as a regularizer for the distribution of latent representations (e.g., distributions of latent object data 202a and/or distributions of latent condition data 204a). The discriminator 126 makes the conditional distribution of the latent object data 202a similar to some predefined prior distribution, e.g. the standard normal distribution of the object data 202.

While performing the methods described herein, the model should meet the following objectives. Variable 3 (e.g., latent object-condition data 206a and latent condition-object data 208a) can be obtained from both the condition 104 and object 102, and thereby the first objective forces the corresponding two latent representations (e.g., latent object-condition data 206a and latent condition-object data 208a) to be as close to each other as possible. The generator of the object, which is the object decoder 122, should be able to reconstruct the object 102 correctly while receiving as input the latent representation of the object (e.g., latent object data 202a) and latent representations of shared information (e.g., latent object-condition data 206a) from both the object encoder 112 and the condition encoder 114. The generator of the condition, which is the condition decoder 124, should be able to reconstruct the condition 104 correctly while receiving as input the latent representation of the object (e.g., latent condition data 204a) and latent representations of shared information (e.g., latent object-condition data 206a) from both the object encoder 112 and the condition encoder 114.

In one embodiment, the architecture can be a single algorithm (e.g., model) or each component may be a separate algorithm. The input for the algorithm is a dataset of data pairs containing representations of an object 102 (e.g., object data 202) and a condition 104 (e.g., condition data 204). In an example, the object 102 is a molecule represented as a string in a SMILES format. A condition is represented as a pair of multidimensional vectors of Gene Expression Profiles (e.g., prior cell state and subsequent cell state). Components of these vectors correspond to the expression of a specific gene. The first vector corresponds to the state of the cell before the molecule was administered (e.g., prior cell state), and the second vector corresponds to the cell state after 24 hours have passed since the administration of the molecule (e.g., subsequent cell state).

The model or architecture 100, 200 contains five components that are neural networks: object encoder 112; condition encoder 114; object decoder 122; condition decoder 124; and discriminator 126. For the SMILES representation, the model can use multilayer Recurrent Neural Networks (RNN) in a form of Long Short-Term Memory (LSTM) or Gated Recurrent Unit (GRU) cells for the object encoder 112 and object decoder 122. For the Gene Expression Profiles, the model can use fully-connected neural networks as the condition encoder 114 and condition decoder 124, as well as the discriminator 126. Thus, these neural networks can be prepared in view of the state of the art with the descriptions provided herein.

The model, including the neural networks, can be trained with training datasets in order to be capable of performing the operations described herein. The training procedure includes two steps executed alternately: (1) a generator step; and (2) a discriminator step. A separate objective function is optimized for one optimization step at each update using an optimization method. An Adam optimizer is an example. Training is terminated when the model loss converges (e.g., object losses module 150 and/or condition losses module 152) or a maximum number of iterations is reached, which can be defined. As such, the iterations can be used to train the neural networks with the training datasets. A result of this training procedure is a generative model, such as the data generator 130, which is capable of producing new objects (e.g., new molecules) approximately matching specified conditions (e.g., prior cell state and subsequent cell state).

Figure 4A:
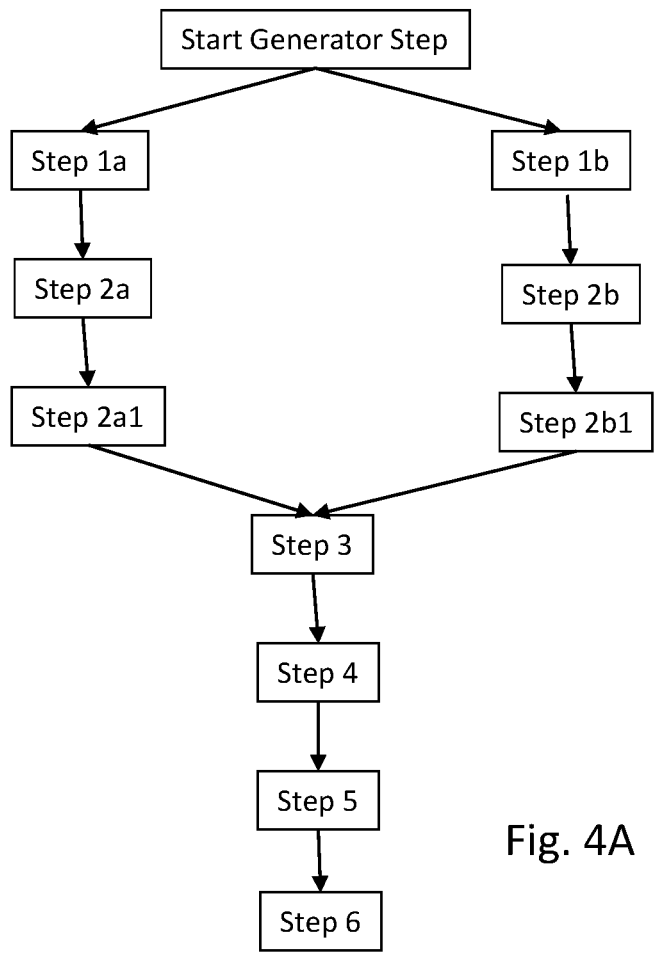
FIG. 4A illustrates an embodiment of a method for a Start Generator Step.

The data generator 130 can be used as described herein and shown in FIG. 4A in a Generator Step. The Generator Step can be performed as follows. Execution of steps 1a and 1b are performed simultaneously and independently. Step 1a can include an object representation (denoted by "x") that is passed as an input to the object encoder 112 in order to obtain a latent representation, which is a pair of multidimensional vectors $z_x$ (latent object data 202a) and $z_{xy}$ (latent object-condition data 206a). Step 1b can include a condition representation (denoted by "y") that is passed as an input to the condition encoder 114 in order to obtain a latent representation, which is a pair of multidimensional vectors $z_y$ (latent condition data 204a) and $z_{yx}$ (latent condition-object data 208a).

FIG. 4 shows that execution of steps 2a and 2b is performed simultaneously and independently. Step 2a includes pair $<z_x, z_{xy}>$ which is passed through the object decoder 122 in order to obtain output, called a reconstructed object (e.g., generated object data 203), which lies in the same domain as the input object. From Step 2a, then Step 2a1 is performed where the reconstructed object (e.g., generated object data 203) is compared with the input object (e.g., object data 202) using a specified similarity measure (e.g., object loss module 150). The deviation of these two objects (e.g., difference between object data 202 and generated object data 203) is called an object reconstruction loss and is denoted by $L_{object}$.

For Step 2b, the same procedure as in Step 2a is applied for the pair of vectors $<z_y, z_{yx}>$ that are passed through the condition decoder 124) to produce a condition reconstruction (e.g., generated condition data 205). From Step 2b, then Step 2b1 is performed where the condition reconstruction (e.g., generated condition data 205) is compared with the input condition (e.g., condition data 204) using a specific similarity measure (e.g., condition module 152). The deviation of these two (e.g., difference between condition data 204 and generated condition data 205) is a calculated deviation called a condition reconstruction loss, denoted by $L_{condition}$.

In Step 3 a deviation in terms of a distance measure (e.g. Euclidean distance) between $z_{xy}$ (e.g., latent object-condition data 206a) and $z_{yx}$ (e.g., latent condition-object data 208a) is computed, such as by the distance comparator 154, and is called a latent deviation loss; one example of the deviation loss is Mean Squared Distance Loss denoted by $L_{MSE}$.

In Step 4 a triplet of vectors $<z_x, z_{xy}, z_y>$ is passed as an input to the discriminator 126, which produces a single number $p_1$. The same procedure is conducted with a triplet of vectors $<z_x, z_{yx}, z_y>$ to produce a single number $p_2$.

A loss function $L_{adv}$ is computed to measure the negative average value of $p_1$ and $p_2$.

In Step 5 a weighted sum of $L_{object}$, $L_{condition}$, $L_{MSE}$ and $L_{adv}$ is computed with predefined weights $w_{object}$, $w_{condition}$, $w_{MSE}$ and $w_{adv}$, resulting in a single number $L_{total} = w_{object} * L_{object} + w_{condition} * L_{condition} + w_{MSE} * L_{MSE} + w_{adv} * L_{adv}$. The lower this number is, the better the model quality is.

Step 6 includes an optimization step that is performed to minimize the $L_{total}$ with respect to parameters of the object encoder 112, condition encoder 114, object decoder 122, and condition decoder 124.

Figure 4B:
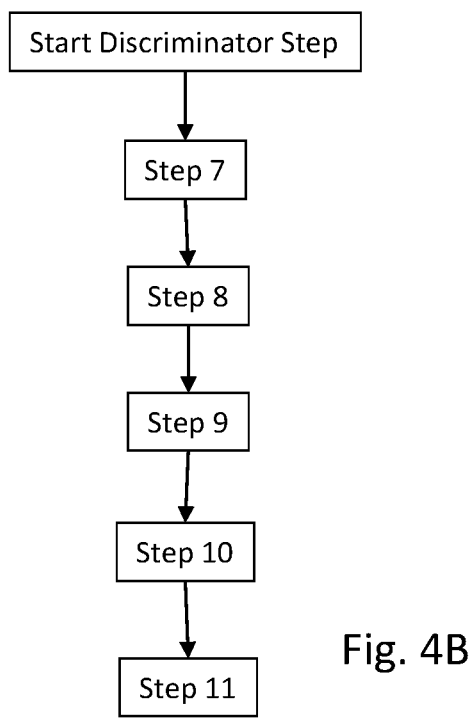
FIG. 4B illustrates an embodiment of a method for a Start Discriminator Step.

After the Generator Step, a Discriminator Step can be performed, such as shown in FIG. 4B. Step 7 is performed after Steps 1a and 1b from the Generator Step are executed, producing multidimensional vectors $z_x$, $z_{xy}$, $z_y$, $z_{yx}$, which are obtained. In Step 8, a value $p_1$ is computed as in Step 4 of the Generator Step, which value $p_1$ is obtained.

In Step 9, a triplet $<z_x, z_{xy}, z_y>$ is sampled from a predefined multidimensional distribution called a reference distribution. A triplet $<z_x, z_{xy}, z_y>$ is passed as an input for the discriminator 126 to produce a single number $p_2$.

In Step 10, a loss function $L_{adv}$ is computed as a difference of $p_1$ and $p_2$. The reference distribution is defined before the model is created. It is required that the distribution over triplet components is independent. In an example, three independent standard normal distributions are used as components of the reference distribution.

In Step 11, an optimizer step is applied to minimize the $L_{adv}$ with respect to parameters of the discriminator 126. This can be performed with an optimizer module.

Figure 4C:
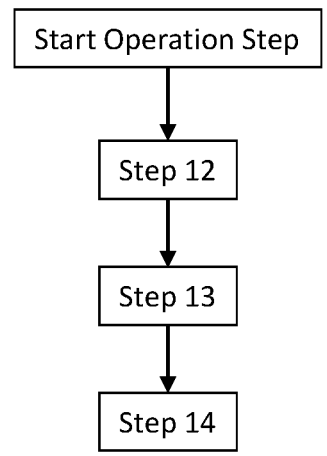
FIG. 4C illustrates an embodiment of a method for a Start Operation Step.

FIG. 4C shows an operation can be performed to produce new objects (e.g., new molecules) with a specified condition. The operation can be started as follows to produce an object that approximately satisfies a condition "y", the following steps are executed. In Step 12, Step 1b from the Generator Step is executed, producing multidimensional vectors $z_y$, $z_{yx}$, which are obtained. Then, Step 13 is performed where a sample $z_x$ is produced from the first component $z_{x'}$ of the reference triplet distribution ($<z_x, z_{xy}, z_y>$). Step 14 includes a pair $<z_x, z_{yx}>$ being passed through the object decoder 122 to produce a novel object, such as x'. Depending on the quality of the model, the specified condition "y" has to be matched approximately, as promoted by the training procedure.

The methodologies provided herein can be performed on a computer or in any computing system, such as exemplified in FIG. 6. As such, the computer can include generative adversarial networks that are adapted for conditional generation of objects (e.g., generated objects), when a known external variable, such as the condition, influences and improves generation and decoding. When data consists of pairs of complex objects, e.g. a supervised dataset with a complex condition, the computing system can create a complex object that is similar to the complex object of the data that satisfies the complex condition of the data. The computing system can process the models described herein that are based on the adversarial autoencoder architecture that learns three independent latent representations: (1) object only information; (2) condition only information, and (3) common information between the object and the condition. The model can be validated or trained with a noisy MNIST dataset, where common information is a digit, and then apply the training to a practical problem of generating fingerprints of molecules with desired effects on a cell. In addition, the model is capable of metric learning between objects and conditions without negative sampling.

The condition usually represents a target variable, such as a class label in a classification problem. In an example, the condition "y" is a complex object itself. For example, drug discovery is used to identify or generate specific molecules with a desired action on human cells, or molecules that bind to some protein. In both cases, the condition (a protein) is far more complex than the object (a candidate molecule for a drug) itself. The models described herein, such as the MIAAE model can be applied to any dataset of two object pairs (x, y), where "x" and "y" are two related complex objects, not necessarily an object and a condition. However, in order to describe the technology, the condition is used for the object, but it is understood that the condition may be a different second complex object. The model is based on AAE that use the GAN framework to shape the distribution of latent variables. The MIAAE model explicitly decouples shared information of the object and condition, forcing the model to split latent representations of the object and the condition into a common part "z" and two separate parts "$z_x$" and "$z_y$", all mutually independent. When a computing process operates with the variation of MIAAE models described herein, the computer can extract common information from the object and the condition, and rank generated objects by their relevance to a given condition and/or rank generated conditions by their relevance to a given object.

The model includes the encoders performing a decomposition of the object data and condition data to obtain the latent representation data. The latent representation data is suitable for conditional generation of generated objects and generated conditions by the generators, and may also be suitable for use in metric learning between objects and conditions. The decomposition of the object and condition into latent representation data helps to better extract relevant features for down-stream tasks, which is important for complex conditions and under lack of data. The sampling procedure can be improved when "$z_x$" and "z" are not independent, and thereby have some dependency. Additionally, the posterior of "$z_x$" given a condition may not be N(0,I) even if the marginal distribution on the latent code is N(0,I). In some aspects, the model can make the posterior tractable by disentangling the object latent code from the condition.

As used herein, the model includes encoders $E_x$ and $E_y$, a generators $G_x$ and $G_y$ (i.e., decoders), and a discriminator D, and "x" is the object, "y" is the condition, and all z correspond to the latent representations produced by the encoders. The MIAAE model can be applied to a problem of mutual conditional generation of "x" and "y" given a dataset of pairs (x, y). Both x and y are assumed to be complex, each containing information irrelevant for conditional generation of the other. The model can include: $z_{x|y}$ as a variable corresponding to data specific for "x" and thereby for the object 102; $z_{y|x}$ as a variable corresponding to data specific for "y" and thereby for the condition 104; and $z_{x \cap y}$ as a variable corresponding to data common between "x" and "y" and thereby common between the object 102 and the condition 104. The data can be a protein-molecule binding dataset with the task of the model to generate molecules for given proteins as well as find proteins that bind to a given molecule. In this case, $z_{y|x}$ is all information about the protein except its binding site, $z_{x \cap y}$ is a common information about which molecules can bind to which binding site, and $z_{x|y}$ represents information about different variations of molecules with the same binding properties. The latent representations are denoted $E_x(x) = (z_x, z_{xy})$, and $E_y(y) = (z_y, z_{yx})$. In some aspects, the model learns $z_{x|y}$ in $z_x$ and $z_{y|x}$ in $z_y$. Preferably, $z_{xy}$ and $z_{yx}$ are the same and equal to $z_{x \cap y}$. The model is processed, such as through iterations by the data generator 130, so that $z_{xy}$ and $z_{yx}$ are substantially equal. The data generator 130 operates for generator $G_x$ being able to reconstruct the object x: $G_x(z_x, z_{xy}) \approx x$ and $G_x(z_x, z_{yx}) \approx x$. The data generator 130 operates for generator $G_y$ being able to reconstruct the object x: $G_y(z_y, z_{xy}) \approx y$ and $G_y(z_y, z_{yx}) \approx x$. The discriminator 126 can distinguish between i.i.d. N(0,I) and $(z_y, z_{xy}, z_y)$ and $(z_y, z_{yx}, z_y)$.

The reconstruction losses for the encoders 112, 114 and decoders 122, 124 are performed, and the adversarial part is defined:

$$\mathcal{L}_{rec} = \lambda_1 \mathbb{E}_{x \sim Pd(x)} \mathcal{L}_x(x, G_x(z_x, z_{xy})) + \lambda_2 \mathbb{E}_{y \sim Pd} \mathcal{L}_y(y, G_y(z_y, z_{yx})) + \mathbb{E}_{x,y \sim Pd}[\lambda_1 \mathcal{L}_x(x, G_x(z_x, z_{yx})) + \lambda_2 \mathcal{L}_y(y, G_y(z_y, z_{xy}))],$$

$$\mathcal{L}_{adv} = \mathbb{E}_{z_{x|y}, z_{x \cap y}, z_{y|x} \sim p(z)}[\log D(z_{x|y}, z_{x \cap y}, z_{y|x})] + \frac{1}{2}\mathbb{E}_{x,y \sim Pd}[\log(1 - D(z_x, z_{xy}, z_y))] + \frac{1}{2}\mathbb{E}_{x,y \sim Pd}[\log(1 - D(z_x, z_{yx}, z_y))]$$

The MSE loss brings $z_{xy}$ and $z_{yx}$ together:

$$\mathcal{L}_{MSE} = \lambda_3 \mathbb{E}_{x,y \sim pd}(x,y) \|z_{xy} - z_{yx}\|_2^2$$

The resulting operation for the MIAAE model is:

$$\min_{G_x, G_y, E_x, E_y} \max_D (\mathcal{L}_{rec} + \mathcal{L}_{adv} + \mathcal{L}_{MSE})$$

A distance metric can be used to measure the similarity of "x" and "y" based on the encodings $z_{xy}$ and $z_{yx}$ to capture common information and allows ranking generated objects "x" accordingly to similarity or relevance to "y," and vice versa.

The MIAAE model can have relaxation of the variational inference approach for the likelihood maximization problem: $\max\theta \log p(x,y|\theta)$. The variational lower bound $\log p(x,y) \geq -KL(q(z|x,y) \| p(z)) + \mathbb{E}q_{(z|x,y)} \log p(x,y|z)$, where $z = (z_x, z_y, z_{xy})$. The second term is bound by reconstruction loss, and with a ratioing the first term becomes:

$$KL(q(z|x,y) \| p(z)) = -\mathbb{E}_{q(z|x,y)}[\log(p(z)/q(z|x,y))] \approx -\mathbb{E}_{q(z|x,y)}[\log(D(z)/(1-D(z)))]$$

D is the discriminator 126. Ideally, q is:

$$q(z | x, y) = q(z_x, z_y, z_{xy} | x, y) =$$
$$\delta(E_m^1(x) - z_x)\delta(E_y^1(y) - z_y)\delta(E_x^2(x) - z_{xy})\delta(E_y^2(y) - z_{xy}) =$$
$$\delta(E_x^1(x) - z_x)\delta(E_y^1(y) - z_y)\delta\left(\frac{E_x^2(x) + E_y^2(y)}{2} - z_{xy}\right)\delta(E_x^2(x) - E_y^2(y)),$$

The $\delta$ is the delta function:

$$E_x(x) = (E_x^1(x), E_x^2(x)), E_y(y) = (E_y^1(y), E_y^2(y))$$

As such, the second parts of the latent representations $E_x(x)$ and $E_y(M)$ coincide exactly with $z_x$ and $z_y$, respectively.

The factor $\delta(E_x^2(x)-E_y^2(y))$ is held approximately, turning into the $\mathcal{L}_{MSE}$ regularizer in the MIAAE loss function. The variational lower bound is maximized with:

$$\max_E \min_D [\mathbb{E}_{z\sim p(z)}\log D(z) -$$
$$\mathbb{E}_q\log(1-D(z)) + \mathbb{E}_q\log p(x,y\mid z) - \lambda_3\|E_x^2(x)-E_y^2(y)\|^2];$$

Here, $q=q(z|x,y)$, where the first two terms represent the weighted $\mathcal{L}_{adv}$, the third term $\mathcal{L}_{rec}$ is a weighted sum of $L_{object}$ and $L_{condition}$, and the last term is weighted $\mathcal{L}_{MSE}$.

In some embodiments, a method for generating an object can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent-condition data to determine a difference; processing the latent object data and latent condition data and one of the latent object-condition data or latent condition-object data with a discriminator to obtain a discriminator value; selecting a selected object from the generated object data based on the generated object data, generated condition data, the difference between the latent object-condition data and latent condition-object data; and the discriminator value; obtaining a physical form of the selected object; and validating the physical form of the selected object.

In some embodiments, the methods can include changing latent object data, latent object-condition data or latent condition-object data, and/or latent condition data based on the discriminator value and difference between object-condition data and condition-object data. The method can also include obtaining an object (e.g., selecting a selected object) based on the generated object data and latent condition-object data from a given condition. The changing latent data refers to the training procedure, where the discriminator value is used. In the generation procedure there is no discriminator value and generated object depends only on the sampled latent object representation and specified latent condition-object representation, which we get from the condition.

In some embodiment, the method can include selecting a selected object from the generated object data based on at least one of the: the generated object data, generated condition data, the difference between the latent object-condition data and latent condition-object data, and the discriminator value. Object and condition data is what is known explicitly. Latent data is unknown and not fixed. Usually the latent data is referred to as the the latent representation, which is just numbers. However, when comparing to object or condition data, these numbers change during the training procedure. There exist some ideal latent representation data that the models and methods described herein tries to find.

In some embodiments, in a generation procedure (e.g., obtaining generated object based on condition), there is no discriminator value or differences used in generation. The generation procedure relies on the training procedure, which includes computing differences and using the discriminator.

In some embodiments, selecting one selected object from the generated objects can be done based on the difference between the latent object-condition data of a generated object with latent condition-object data.

In some embodiments, the method can include: comparing the generated object data with the object data; and selecting a selected generated object data that is less than a threshold object difference between the generated object data and the object data.

In some embodiments, the method can include: comparing the generated condition data with the condition data; and selecting a selected generated condition data that is less than a threshold condition difference between the generated condition data and the condition data.

In some embodiments, the method can include: selecting the selected object that corresponds with the selected generated object data or that corresponds with the selected generated condition data.

In some embodiments, the method can include: preparing the physical form of the selected object; and testing the physical object with the condition.

In some embodiments, the method can include: the obtaining of the physical form of the selected object includes at least one of synthesizing, purchasing, extracting, refining, deriving, or otherwise obtaining the physical object; and/or the testing includes assaying the physical form of the selected object in a cell culture; and/or assaying the physical form of the selected object by genotyping, transcriptome-typing, 3-D mapping, ligand-receptor docking, before and after perturbations, initial state analysis, final state analysis, or combinations thereof.

In some embodiments, the method can include: the processing with the object encoder and the processing with the condition encoder are performed simultaneously and independently; and/or the processing with the object decoder and the processing with the condition decoder are performed simultaneously and independently.

In some embodiments, difference between the latent object-condition data and the latent condition-object data is a latent deviation loss $L_{MSE}$ of an Euclidean distance between the latent object-condition data and latent condition-object data. In some aspects, the discriminator value is in a range of [0,1], and a loss function of the difference between the discriminator value and 1 is determined as the $L_{adv}$.

In some embodiments, the method can include: defining the latent object data as $L_{object}$ and defining a weighting of the latent object data as $W_{object}$; defining the latent condition data as $L_{condition}$ and defining a weighting of the latent condition data as $W_{condition}$; defining a weighting of the $L_{MSE}$ as $W_{MSE}$; defining a weighting of the $L_{adv}$ as $W_{adv}$; and calculating a weighted sum as an $L_{total}$; and determining whether $L_{total}$ is below a threshold, when the $L_{total}$ is below the threshold, the selected object is selected. In some aspects, $L_{total}=W_{object}*L_{object}+W_{condition}*L_{condition}+W_{MSE}*L_{MSE}+W_{adv}*L_{adv}$.

In some embodiments, the latent object-condition data is substantially equal to the latent condition-object data.

In some embodiments, the method can include: assuming the object is complex; and assuming the condition is complex.

In some embodiments, the method can include the dataset being a pairs dataset of pairs (x,y) wherein the object is x and the condition is y, the pairs dataset including: $z_{x|y}$ is a variable corresponding to data specific for x and thereby for the object; $z_{y|x}$ is a variable corresponding to data specific for y and thereby for the condition; and $z_{x\cap y}$ is a variable corresponding to data common between x and y and thereby common between the object and the condition.

In some embodiments, the dataset includes data for molecule-protein binding, $z_{x|y}$ includes data for one or more molecules that bind with a target protein; $z_{y|x}$ includes data for different molecules with similar binding properties to the target protein; and $z_{x \cap y}$ includes data linking one or more specific molecule to one or more specific binding sites of a target protein.

In some embodiments, the dataset includes data for molecules, cell states prior to interacting with a molecule, and cell states subsequent to interacting with the molecule; $z_{x \cap y}$ includes necessary data to describe what types of molecules induce the same cell state changes; $z_{x|y}$ includes data on variation of molecules that cause the same change in a transcriptome of the a cell; $z_{y|x}$ includes data for cellular processes unrelated to the molecule-induced changes, e.g. a non-effective molecule had no influence on a cell, but there are still transcriptome changes as cellular processes are not static.

In some embodiments, the selected object is a molecule, the obtaining of the physical form includes synthesizing the molecule, and the validating includes: obtaining transcriptome data of a cell prior to interacting with the molecule; and obtaining transcriptome data of the cell subsequent to interacting with the molecule.

In some embodiments, the method can include determining whether the molecule satisfies the condition.

In some embodiments, the method can include determining the molecule is similar to one or more molecules in the object data; and determining the molecule has an activity similar to the one or more molecules in the condition data.

In some embodiments, the method can include: determining the molecule is distinct from other molecules with other mechanisms of action.

The method may also be performed with various other steps or substeps. In some aspects, the method can include selecting useful object data, useful condition data, and useful object-condition data and/or useful condition-object data. In some aspects, the encoded object-condition data is substantially equal to the encoded condition-object data. In some aspects, the method can include: assuming the object is complex; and assuming the condition is complex.

In some aspects, the dataset 110 is a pairs dataset for the object 102 and the condition 104 having: object data 202 only related to the object 102; condition data 204 only related to the condition 104; and object-condition data 206 and/or condition-object data 208 related to the object 102 and the condition 104.

In some aspects, the dataset 110 is a pairs dataset 110 for the object 102 and the condition 104 having: object only data only related to the object 102 with no relation to the condition 104; and condition only data only related to the condition 104 with no relation to the object 102.

In some aspects, the dataset 110 is a pairs dataset of pairs (x,y) wherein the object 102 is "x" and the condition 104 is "y", the pairs dataset including: $z_{x|y}$ as a variable corresponding to data specific for x and thereby for the object 102; $z_{y|x}$ as a variable corresponding to data specific for y and thereby for the condition 104; and $z_{x \cap y}$ as a variable corresponding to data common between x and y and thereby common between the object 102 and the condition 104.

In some aspects, $z_{x|y}$ includes data on variation of molecules that bind with a target protein; $z_{y|x}$ includes data on the protein excluding target protein binding sites with the molecule; and $z_{x \cap y}$ includes data on binding properties, linking one or more specific molecules to one or more specific binding sites of a target protein.

In some embodiments, the dataset 110 includes data for molecule-protein binding. In some aspects, the method can include configuring an object decoder 122 that generates molecules that bind with a given protein. In some aspects, the method can include configuring a condition decoder 124 that generates proteins for a given molecule.

In some aspects, the method can include processing the dataset 110 to extract object data 202 and object-condition data 206 and/or condition-object data 208; and processing the dataset 110 to extract condition data 204 and condition-object data 208 and/or object-condition data 206. In some aspects, the method can include processing the dataset 110 to decouple encoded object data and encoded object-condition data and/or encoded condition-object data from the encoded condition data; and processing the dataset 110 to decouple encoded condition data and encoded condition-object data and/or encoded object-condition data from the encoded object data.

In some embodiments, the method can include comparing the encoded object-condition data with the encoded condition-object data; and determining the encoded object-condition data 206a and the encoded condition-object data 208a to be about the same, when the same, processing the encoded object-condition data.

In some embodiments, the method can include processing the encoded object data to extract useless object data and extract useful object data; processing the encoded condition data to extract useless condition data and extract useful condition data; and processing the encoded object-condition data and/or encoded condition-object data to extract useless object-condition data and/or useless condition-object data and extract useful object-condition data and/or useful condition-object data.

In some embodiments, the method can include discarding the useless object data, useless condition data, and useless object-condition data and/or useless condition-object data. In some aspects, the method can include selecting useful object data, useful condition data, and useful object-condition data and/or useful condition-object data.

Additionally, the model can be modified as described herein or with the knowledge of one of ordinary skill in the art. In one aspect, different methods can be used to promote the defined distribution of triplets $<z_x, z_{xy}, z_y>$ and $<z_x, z_{yx}, z_y>$. These include using Kulback-Leibler divergence instead of the discriminator, as it is done in Variational Autoencoders. Also, discriminators of some models, including Wasserstein GAN, return values not from [0, 1], but from an unbounded range. As such, the recitation of processing with the discriminator can include unbounded values and different objectives to promote the defined distribution, or the discriminator can be replaced with Kulback-Leibler divergence term in the generator.

Examples

First, the models are validated on the noisy MNIST dataset that contains paired images of the same digit with noise and rotations added to only one; common information between two objects is only digit identity. The models do not use the label, but it is used for evaluation. We compare the models on conditional generation quality. The condition is a noisy image, and the object is a clear image of the same digit, not necessarily with the same style or tilt. The models are expected to extract label information from the condition and sample objects with the correct label. The train-validation-test split contains 50K, 10K, and 10K samples respectively. We set the batch size to 64, learning rate to 0.0005, and used the Adam optimization algorithm with updates on three batches for the discriminator.

Encoder and decoder architectures are the same for all models: $|z_x|=|z_y|=12$, $|z|=4$, the encoder has 2 convolutional layers with 2D dropout followed by 3 fully-connected layers with batch normalization and dropout 0.2, and the discriminator has 2 hidden layers with 1024 units. The reconstruction coefficient is set to 10 and MSE and triplet coefficients are at 1. In the case of VCCA, the KL divergence coefficient is set so that its reconstruction quality matches MIAAE.

TMIAAE is a modified MIAAE model that adds negative sampling and triplet loss to the objective function. DLSAAE is a modified model that extends LSAAE with decoupling to provide the decoupled latent supervised adversarial autoencoder. The LSAEE is the latent supervised adversarial autoencoder.

Figure 1B:
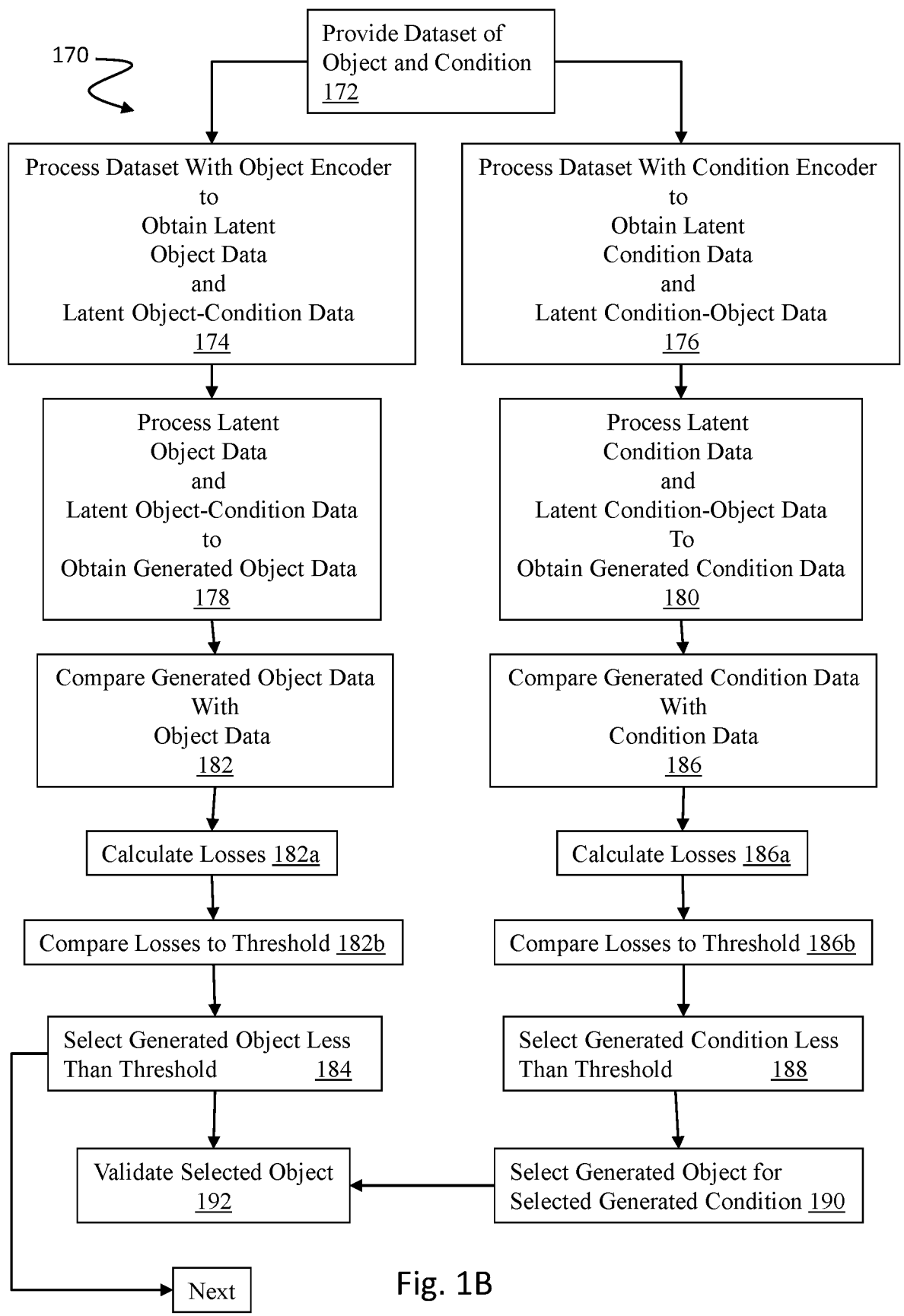
FIG. 1B illustrates an embodiment of a method for operation of the MIAAE of FIG. 1A.
Figure 8A:
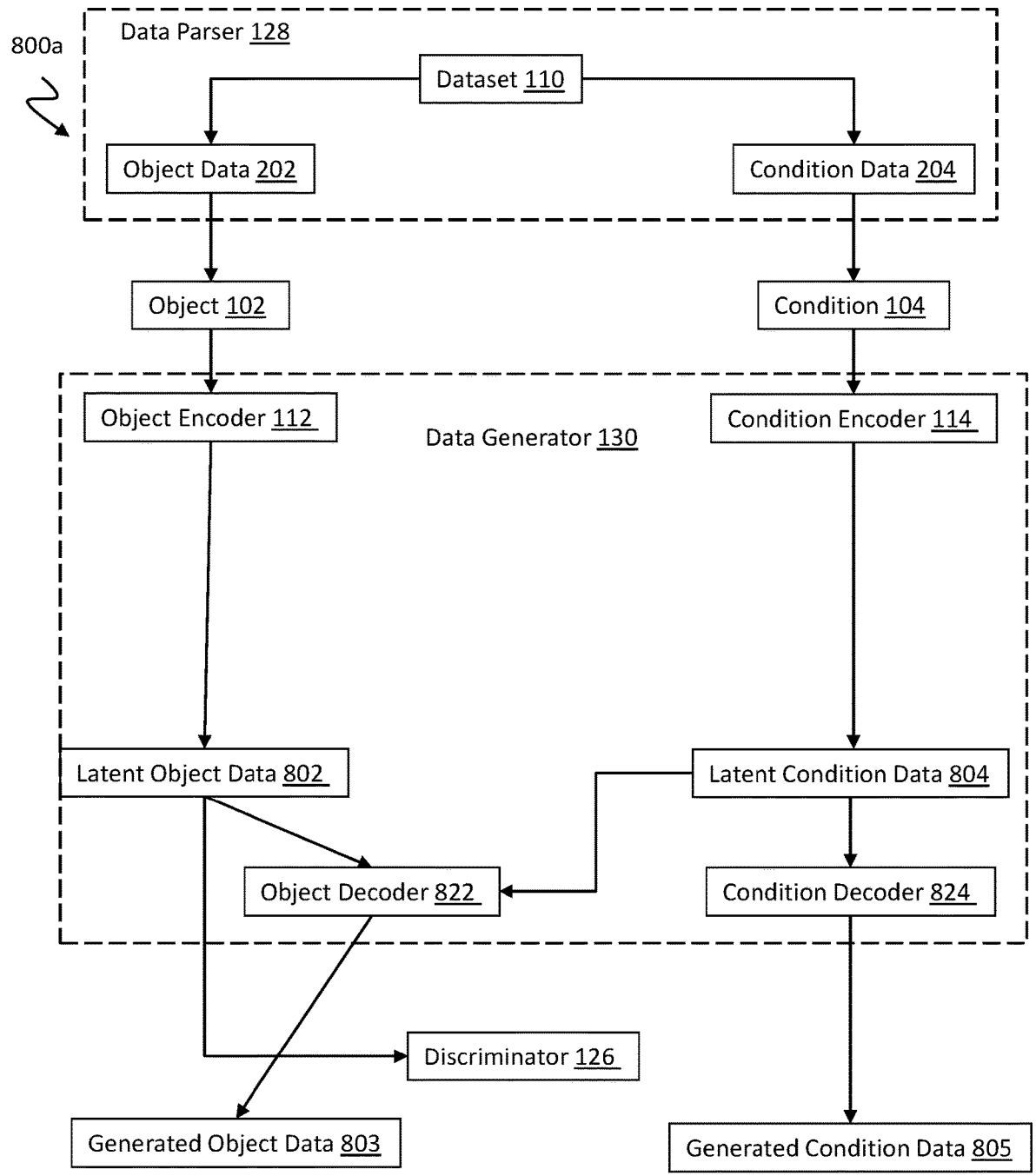
FIG. 8A illustrates an embodiment of a Latent Supervised Information Adversarial Autoencoder (LSAAE).

An embodiment of LSAAE 800a is shown in FIG. 8A. Some of the LSAAE is similar to the MIAAE of FIG. 1, up to the object encoders, which produce latent object data 802 and latent condition data 804. The latent object data 802 and latent condition data 804 are provided to the object decoder 822, which produces the generated object data 803. The condition decoder 824 only receives the latent condition data 804 as input and provides the generated condition data 805. The discriminator 126 receives the latent object data 802 as the only input, and thereby the discriminator 126 is N(0,I) vs $z_x$.

Figure 8B:
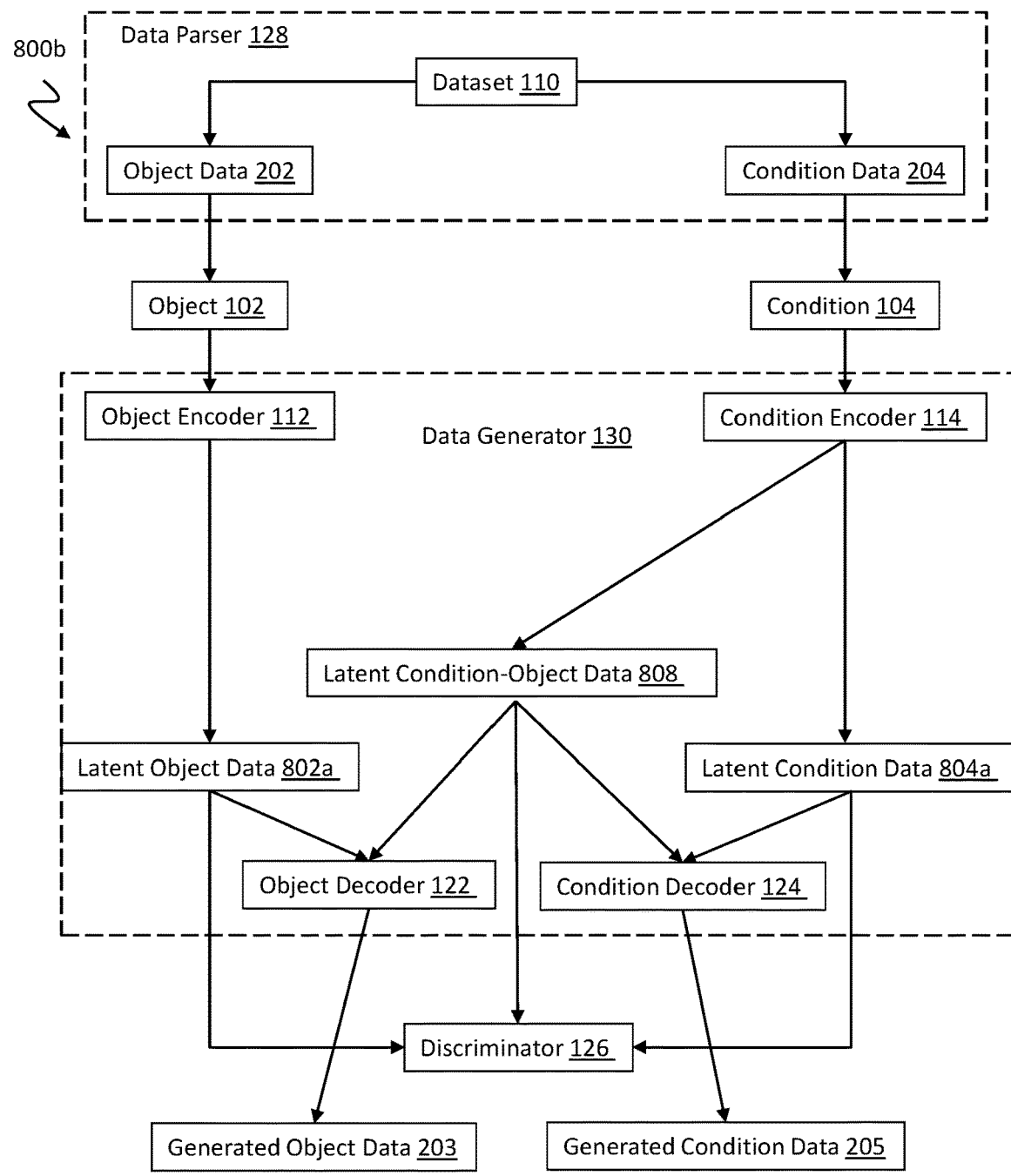
FIG. 8B illustrates an embodiment of a Decoupled Latent Supervised Information Adversarial Autoencoder (DL-SAAE).

An embodiment of DLSAAE 800b is shown in FIG. 8B. Some of the DLSAAE is similar to the MIAAE of FIG. 1A, up to the object encoders, which object encoder 112 produces the latent object data 802a, and the condition encoder 114 produces the latent condition-object data 808 and the latent condition data 804a. The latent object data 802a is provided to the object decoder 122 and the discriminator 126. The latent condition-object data 808 is provided to the object decoder 112, discriminator 126, and condition decoder 124. The latent condition data 804a is provided to the condition decoder 124 and the discriminator. The discriminator 126 is <N(0,I), $z_{yx}$, $z_y$> versus <$z_x$, $z_y$>.

TABLE 1

Noisy MNIST Generation

| Model | Acc.(%, ↑) gen'd → label | NLL(↓) gen'd → label | Triplet MSE(↓) (cond, gen'd) → MSE |
|---|---|---|---|
| SAAE | 38.6 | 2.364 | 6.365 |
| LSAAE | 22.1 | 3.642 | 7.162 |
| VCCA | 9.9 | 5.164 | 8.044 |
| MIAAE (ours) | 70.6 | 0.902 | 5.421 |
| TMIAAE (ours) | 75.2 | 0.792 | 5.308 |
| DLSAAE (ours) | 10 | 5.096 | 7.974 |

TABLE 2

Mutual Information Estimation
Table 2: Mutual Information Estimation

| Model | MINE (↓) MI($z_x$, $z_{yx}$) | NLL (↑) $z_x$ → label |
|---|---|---|
| SAAE | 0.639[a] | 0.371 |
| LSAAE | 1.364 | 0.288 |
| VCCA | 0.814 | 0.482 |
| MIAAE (ours) | 0.664 | 1.163 |
| TMIAAE (ours) | 0.767 | 1.054 |
| DLSAAE (ours) | 0.317 | 0.229 |

[a] For this model we use MI($z_x$, y)

The results are shown in Table 1. The digit classifier was trained on plain MNIST images. Based on predictions on generated images (10 per example), the report of accuracy and negative log likelihood (NLL) are provided. Another approach is to use a triplet model that learns a common metric between noisy images and real ones. In the latent space, MSE between condition and generated objects is a good estimate of generation quality, as the protocol used negative sampling of real images with correct digits. In addition, an estimate is made of the mutual information between $z_x$ and $z_{yx}$ with Mutual Information Neural Estimator (MINE). The $z_x$ and $z_{yx}$ are independent. Since the common information is the digit, the model assess how much of it is in $z_x$ by training another classifier on the latent space; classifier performance exactly assesses what is needed for conditional generation, whereas MI is not restricted to label information. Moreover, for SAAE, the MINE estimator takes the entire 784-dimensional vector y, whereas classifier performance was measured on $z_x$ with the same dimension for all models.

Figure 5:
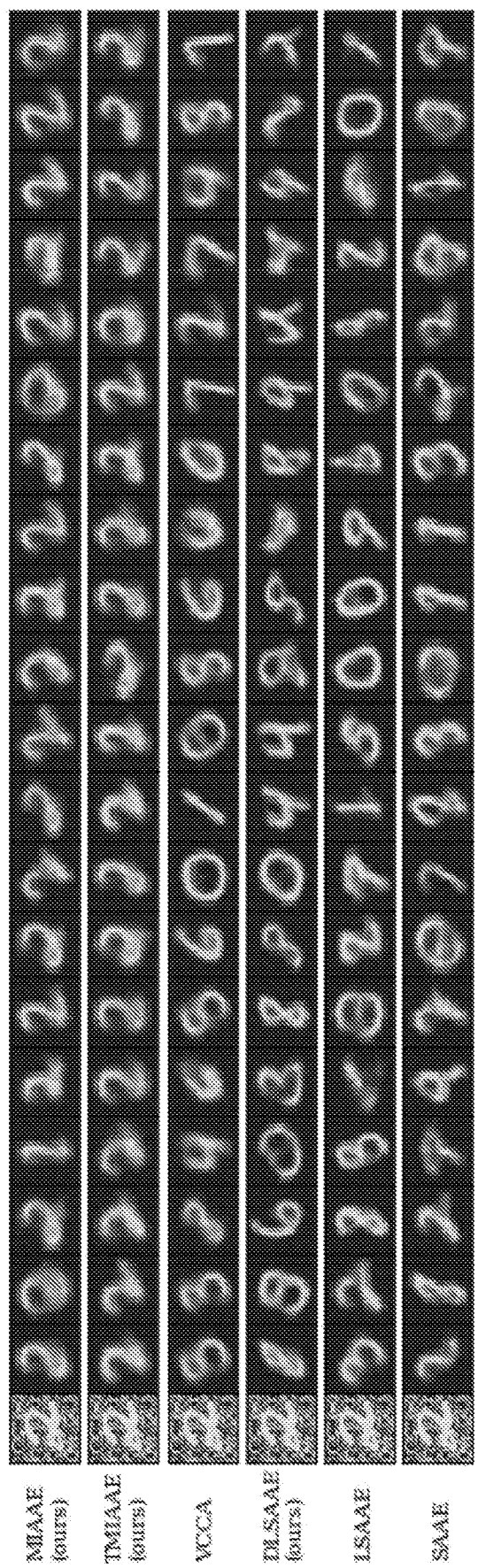
FIG. 5 is an image obtained for various models, including MIAAE, for random samples for a fixed condition.

Table 2 shows both the estimated lower bound of MINE and NLL of the classifier on the test data. MIAAE and TMIAAE contain less information about digit identity, and DLSAAE has almost all x∩y in $z_x$, based on NLL. The DLSAAE showed smaller values of MINE estimator, along with poor reconstruction of y. Thus, in the case of DLSAAE, $z_x$ and $z_{yx}$ are relatively independent, but $z_x$ does contain x∩y, which means $z_{yx}$ and $z_y$ indeed do not cover all information from y. This situation does not happen in MIAAE because of extracting x∩y from both x and y. Finally, FIG. 5 shows how disentanglement of $z_x$, and $z_{yx}$ actually helps to improve generation quality. MIAAE and TMIAAE generate correct digits that satisfy the condition.

Having validated MIAAE on a synthetic problem where common information is known, we compare the models described herein on a more realistic dataset for molecule generation. Molecules are represented with MACCS fingerprints, binary 166-dimensional vectors. The model uses the standard binary cross-entropy as a reconstruction loss, but the final goal is to optimize the Tanimoto similarity coefficient commonly used in drug discovery; for binary vectors it coincides with Jaccard similarity:

$$T(m_1, m_2) = (m_1 \& m_2)/(m_1 | m_2)$$

Where $m_1$ and $m_2$ are binary fingerprints and & and | are the bitwise AND and OR operations, respectively.

TABLE 3

LINCS L1000 dataset details

| Cell Line | # pairs | # $cs_a$ per pair | # $cs_b$ per pair | # m |
|---|---|---|---|---|
| VCAP | 16929 | 3.69 | 48.63 | 6383 |
| A375 | 8635 | 2.93 | 44.05 | 2908 |

TABLE 3-continued

LINCS L1000 dataset details

| Cell Line | # pairs | # $cs_a$ per pair | # $cs_b$ per pair | # m |
|---|---|---|---|---|
| MCF7 | 15278 | 3.57 | 47.7 | 6358 |
| A549 | 13566 | 2.71 | 41.58 | 5699 |

TABLE 4

Choice of hyperparameters

| Hyperparameter | Value |
|---|---|
| Molecular Enc. | IN(166)-512-128-OUT(12 + 8) |
| Cellular Enc. | IN(978)-512-OUT(64) |
| Difference Enc. | IN(129)-128-OUT(12 + 32) |
| Discriminator | IN-512-512-OUT(1) |
| Batch Norm. | No |
| Activation Func. | LeakyReLU |
| Dropout | 0.5 for $\|z_{xy} - z_{yx}\|^2$ only |
| Learning Rate | 0.0001 |

TABLE 5

External validation molecules

| Cell Line | Gene Inhibitors | #Inhibitors/ #Effective Molecules |
|---|---|---|
| VCAP | HSP90 | 8/99 |
| A375 | BRAF | 149/1027 |
| MCF7 | HSP90 | 154/6520 |
| A549 | EGFR (HER1) | 159/6335 |

The training uses a transcriptome dataset from the LINCS L1000 project, which contains measurements of cell states before and after the cell reacts with a molecule at a given dose. The cell states are represented as gene expression profiles. There are several cell types, called cell lines, and the experimental data guarantee that cells within each cell line are exactly the same, such as breast cancer cells from one human. Thus, the data consist of several datasets of molecules applied to different cell lines.

For each cell line, the training set contains replicated experiments characterized by quadruples (m, $\eta$, $\{cs_b\}$, $\{cs_a\}$), where m is a small molecule, $\eta$, is its molar concentration, and $cs_b$ and $cs_a$ are cell states before and after the molecular perturbation applied to a cell, with:

$CS_a$, $CS_b \in \mathbb{R}^{978}$, $m \in \{0,1\}^{166}$, $\eta \in \mathbb{R}$.

Replication of experiments and abundance of control cells have led to significant data augmentation. Since the model has several pairs ($cs_b, cs_a$) for each experiment, the model samples them randomly at each iteration. This sampling is basically a form of data augmentation, which blows the about 15000 experiments in the dataset up to about 1.5 million training examples for each cell line. Table 3 shows the datasets description used in the experiments. It highlights a common problem in drug discovery: although there are large datasets for the condition, there are only a few molecules with known or tested effects; in drug discovery, conditions are often more complex and diverse than objects. Therefore, to improve the molecular autoencoder the model utilizes a large unlabeled dataset of drug-like molecules. The model uses a cleaned $Z_{inc}$ dataset that contains about 3 million unique fingerprints.

Figure 7:
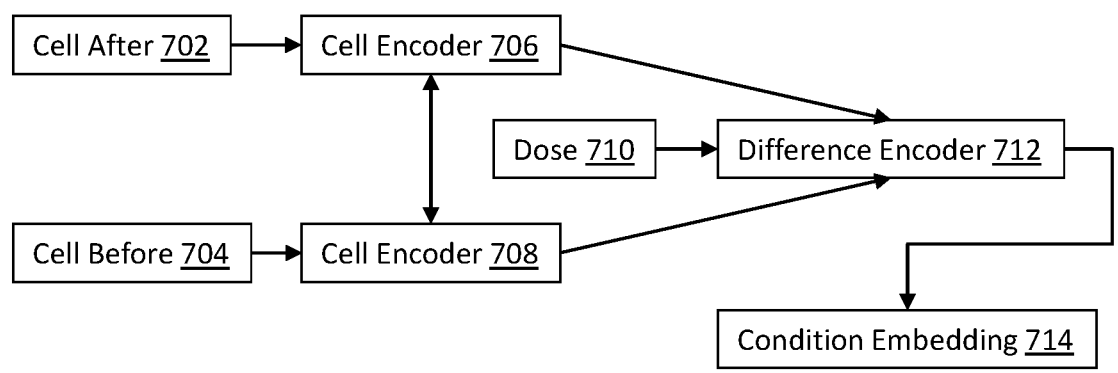
FIG. 7 illustrates architecture of the condition encoder for changes in a transcriptome.

The model train-validation-test split ensures that molecules are disjoint. The model used batch size 64 for the labeled dataset and 512 for the unlabeled. The model used the Adam optimizer with learning rate 0.0001. The same parameters and architecture were used for all models when possible. The data to summarize the resulting hyperparameters is in Table 4. The model uses different discriminators for supervised and unsupervised data, and performs supervised and unsupervised batches alternately. In order to extract features from the complex condition ($\eta$, $cs_b$, $cs_a$), the model used encoder architecture shown in FIG. 7 having: the cell after 702 (data), cell before 704 (data), cell encoder 706, cell encoder 708, the dose 710, the difference encoder 712, and the condition embedding 714. The model reduces the number of parameters by sharing weights in cell encoders. The difference encoder takes the dose and latent representations of $cs_a$ and $cs_b$ as input.

The model validates conditional generation using already known effective molecules for each cell line. These molecules have different mechanisms of action, so the protocol can choose a group of molecules with the same effect: inhibition of a specific protein. The condition is a cell state change obtained from known gene inhibitors in the dataset. One would expect that generation for the condition will produce new molecules with the same action, similar to or containing known inhibitors, and less similar to other non-related drugs. Table 5 shows the details of the test dataset, where the protocol chose the most common group of gene inhibitors for each cell line. The protocol also obtained 6766 additional fingerprints of approved drugs from DrugBank to count as non-related drugs. Thus, for each cell line, the model has the sets of specific inhibitors Mi and other drugs Mo. Mo contains drugs with different mechanism of action, but effective on the cell line. The model generates molecules G for a condition from inhibitors, so the protocol defines the following metrics to assess how similar C and Mi are: (1) $AUC_{GMean}$ ranks generated molecules by mean Tanimoto similarity to Mi and Mo; the metric is ROC-AUC with the target equal to 1 for the set Mi and 0 for Mo, so the perfect ROC-AUC of 1 would mean that every generated molecule is on average more similar to Mi rather than to Mo; (2) $AUC_{Rmax}$ ranks Mi and Mo by maximum Tanimoto similarity to generated molecules G; the quality metric is ROC-AUC with the same target 1 for the set Mi and 0 for Mo, so the perfect ROC-AUC of 1 would mean that all molecules from G have their nearest neighbor from Mi rather than from Mo.

The process excluded inhibitors from training and generated $10^5$ unique fingerprints for each cell line. Results of this comparison are shown in Table 6. For almost all cell lines, MIAAE has generated better fingerprints.

TABLE 6

External validation results

| Cell Line | Metrics (↑) | SAAE | LSAAE | MIAAE | DLSAAE |
|---|---|---|---|---|---|
| VCAP | $AUC_{GMean}$ | 0.715 | 0.839 | 0.715 | 0.702 |
|  | $AUC_{RMax}$ | 0.679 | 0.705 | 0.613 | 0.563 |
| A375 | $AUC_{GMean}$ | 0.681 | 0.735 | 0.913 | 0.813 |
|  | $AUC_{RMax}$ | 0.646 | 0.672 | 0.722 | 0.657 |
| MCF7 | $AUC_{GMean}$ | 0.735 | 0.743 | 0.804 | 0.761 |
|  | $AUC_{RMax}$ | 0.645 | 0.645 | 0.674 | 0.621 |
| A549 | $AUC_{GMean}$ | 0.632 | 0.677 | 0.725 | 0.676 |
|  | $AUC_{RMax}$ | 0.593 | 0.569 | 0.621 | 0.611 |

The object-condition correspondent can be ranked. As for the ranking quality obtained on noisy MNIST and LINCS datasets, it is expected that the triplet model to provide the best quality of metric learning. The protocol denotes by MSE+ and MSE− distances between an anchor and a positive or a negative example, respectively. For each object-condition pair, the model samples negative objects randomly from the same distribution, and MSE+<MSE− means that the pair is ordered correctly. The protocol defines two ranking quality metrics: (1) $Q_{pair}$ is the fraction of correctly ordered positive-negative pairs (very similar to the triplet loss); (2) $AUC_{MSE}$ is the ROC-AUC metric with target 0 for all MSE+ values and 1 for MSE− values; optimizing $AUC_{MSE}$ would mean bringing all MSE+ values closer to 0 and have larger MSE− values than MSE+.

Experimental results on ranking in Table 7 reveal the same pattern: the triplet model is the best by $Q_{pair}$ and TMIAAE by $AUC_{MSE}$. On noisy MNIST, MIAAE shows good results compared to the triplet model even without negative sampling. On LINCS datasets, the triplet model has an average≈Qpair 91% over reported cell lines, and MIAAE has an average value≈75%. On the other hand, MSE+ values are relatively small compared to each other, which gives MIAAE a big advantage over a simple triplet network for the $AUC_{MSE}$ metric. In both cases, adding triplet loss to the MIAAE model (TMIAAE) improves the metrics a little, but still does not achieve the best triplet $Q_{pair}$ due to other constraints imposed for better conditional generation. Thus, MIAAE implicitly learns a metric between objects and conditions as a by-product, and adding explicit negative sampling with triplet loss does not improve ranking quality drastically.

to I rather than to O. We estimate the performance by measuring the average Tanimoto similarity of generated objects to objects from O (class 0) and from I (class 1). In the ideal case, the similarity to objects from I will be greater than similarity to objects from O. We measure the ranking with ROC-AUC metric, getting 91.3% on A375 cell line, 80.4% on MCF7, 72.5% on A549 and 71.5% on VCAP, indicating a good performance of the proposed model.

For the models, and processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

TABLE 7

Comparison of ranking quality $Q_{pair}$

| | $Q_{pair}$ | | | $AUC_{MSE}$ | | |
|---|---|---|---|---|---|---|
| Dataset | Triplet | MIAAE | TMIAAE | Triplet | MIAAE | TMIAAE |
| noisy MNIST | 97.1% | 94.3% | 95.9% | 0.941 | 0.939 | 0.956 |
| LINCS VCAP | 93.4% | 77.8% | 80.8% | 0.559 | 0.768 | 0.787 |
| LINCS A375 | 92.7% | 74.9% | 79% | 0.707 | 0.739 | 0.781 |
| LINCS MCF7 | 86.7% | 71.6% | 75.3% | 0.538 | 0.707 | 0.742 |
| LINCS A549 | 91.2% | 75.5% | 79.2% | 0.59 | 0.747 | 0.787 |

The embodiments of the models described herein generate molecules as validated by satisfying a specified condition. As a condition, the protocol uses gene profiles before and after administering a molecule that inhibit a specific protein. The goal is to show that generated molecules are similar to known inhibitors (not present in the training dataset) and distinct from molecules with other mechanisms of action.

The protocol used 166-dimensional binary vectors called MACCS fingerprints as a molecular representation, since it is well suited for the similarity comparison.

The validation procedure was performed as follows. We chose MCF7, A375, A549 and VCAP cancerous cell lines along with currently known effective molecules for each cell line. Among those effective molecules there are specific inhibitors of HSP90, BRAF, HSP90, EGFR (HER1) genes for each line respectively. We obtain condition for inhibitors of the gene on the cell line, and generate 100,000 molecular fingerprints X that follow one condition for each cell line (inhibition of the protein). We compute the similarity of generated molecules to the group of inhibitors I and to other molecules O, which includes other effective drugs on the cancerous cell line, but with different mechanism of action. A good model produces objects that are similar on average In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

FIG. 6 shows an example computing device 600 (e.g., a computer) that may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In some embodiments, a computer program product can include a non-transient, tangible memory device having computer-executable instructions that when executed by a processor, cause performance of a method that can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent-condition data to determine a difference; processing the latent object data and latent condition data and one of the latent object-condition data or latent condition-object data with a discriminator to obtain a discriminator value; selecting a selected object from the generated object data based on the generated object data, generated condition data, and the difference between the latent object-condition data and latent condition-object data; and providing the selected object in a report with a recommendation for validation of a physical form of the object. The non-transient, tangible memory device may also have other executable instructions for any of the methods or method steps described herein. Also, the instructions may be instructions to perform a non-computing task, such as synthesis of a molecule and or an experimental protocol for validating the molecule. Other executable instructions may also be provided.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A method for generating an object, the method comprising:
   providing a dataset having object data for an object and condition data for a condition;
   processing the object data of the dataset to obtain latent object data and latent object-condition data with an object encoder;
   processing the condition data of the dataset to obtain latent condition data and latent condition-object data with a condition encoder;
   processing the latent object data and the latent object-condition data to obtain generated object data with an object decoder;
   processing the latent condition data and latent condition-object data to obtain generated condition data with a condition decoder;
   comparing the latent object-condition data to the latent condition-object data to determine a difference;
   processing the latent object data and latent condition data and one of the latent object-condition data or latent condition-object data with a discriminator to obtain a discriminator value;
   obtaining better latent object data, latent object-condition data or latent condition-object data, and/or latent condition data based on the discriminator value, difference between the latent object-condition data and latent condition-object data, and difference between object with generated object and condition with generated condition;
   selecting a selected object based on the generated latent object data and latent condition-object data from a given condition;
   obtaining a physical form of the selected object; and
   validating the physical form of the selected object.

2. The method of claim 1, comprising performing:
   comparing the generated object data with the object data; and
   selecting a selected generated object data that is less than a threshold object difference between the generated object data and the object data.

3. The method of claim 2, comprising performing:
   comparing the generated condition data with the condition data; and
   selecting a selected generated condition data that is less than a threshold condition difference between the generated condition data and the condition data.

4. The method of claim 3, comprising selecting the selected object that corresponds with the selected generated object data or that corresponds with the selected generated condition data.

5. The method of claim 1, further comprising:
   preparing the physical form of the selected object; and
   testing the physical object with the condition.

6. The method of claim 5, wherein:
the obtaining of the physical form of the selected object includes at least one of synthesizing, purchasing, extracting, refining, deriving, or otherwise obtaining the physical object; and/or
the testing includes assaying the physical form of the selected object in a cell culture; and/or
assaying the physical form of the selected object by genotyping, transcriptome-typing, 3-D mapping, ligand-receptor docking, before and after perturbations, initial state analysis, final state analysis, or combinations thereof.

7. The method of claim 1, wherein:
the processing with the object encoder and the processing with the condition encoder are performed simultaneously and independently; and/or
the processing with the object decoder and the processing with the condition decoder are performed simultaneously and independently.

8. The method of claim 1, wherein the difference is a latent deviation loss $L_{MSE}$ of an Euclidean distance between the latent object-condition data and latent condition-object data.

9. The method of claim 8, wherein the discriminator value is in a range of [0,1], and a loss function of the difference between the discriminator value and 1 is determined as the $L_{adv}$.

10. The method of claim 9, further comprising:
defining the latent object data as $L_{object}$ and defining a weighting of the latent object data as $W_{object}$;
defining the latent condition data as $L_{condition}$ and defining a weighting of the latent condition data as $W_{condition}$;
defining a weighting of the $L_{MSE}$ as $W_{MSE}$;
defining a weighting of the $L_{adv}$ as $W_{adv}$;
calculating a weighted sum as an $L_{total}$; and
determining whether $L_{total}$ is below a threshold, when the $L_{total}$ is below the threshold, the selected object is selected,
wherein:

$$L_{total}=W_{object}*L_{object}+W_{condition}*L_{condition}+W_{MSE}*L_{MSE}+W_{adv}*L_{adv}.$$

11. The method of claim 1, wherein the latent object-condition data is substantially equal to the latent condition-object data.

12. The method of claim 1, comprising:
assuming the object is complex; and
assuming the condition is complex.

13. The method of claim 1, wherein the dataset is a pairs dataset of pairs (x,y) wherein the object is x and the condition is y, the pairs dataset including:
$z_{x|y}$ as a variable corresponding to data specific for x and thereby for the object;
$z_{y|x}$ as a variable corresponding to data specific for y and thereby for the condition; and
$z_{x \cap y}$ as a variable corresponding to data common between x and y and thereby common between the object and the condition.

14. The method of claim 13, wherein the dataset includes data for molecule-protein binding,
$z_{x|y}$ includes data for one or more molecules that bind with a target protein;
$z_{y|x}$ includes data for different molecules with similar binding properties to the target protein; and
$z_{x \cap y}$ includes data linking one or more specific molecules to one or more specific binding sites of a target protein.

15. The method of claim 13, wherein the dataset includes data for molecules, cell states prior to interacting with a molecule, and cell states subsequent to interacting with the molecule;
$z_{x \cap y}$ includes data that describe molecule-cell interaction;
$z_{x|y}$ includes data on variation of molecules that cause the same change in a cell transcriptome; and
$z_{y|x}$ includes data for a transcriptome that is not related to the molecule-induced changes.

16. The method of claim 1, wherein the selected object is a molecule, the obtaining of the physical form includes synthesizing the molecule, and the validating includes:
obtaining transcriptome data of a cell prior to interacting with the molecule; and
obtaining transcriptome data of the cell subsequent to interacting with the molecule.

17. The method of claim 16, further comprising determining whether the molecule satisfies the condition.

18. The method of claim 17, comprising:
determining the molecule is similar to one or more molecules in the object data; and
determining the molecule has an activity similar to the one or more molecules in the condition data.

19. The method of claim 18, comprising determining the molecule is distinct from other molecules with other mechanisms of action.

20. A computer program product comprising:
a non-transient, tangible memory device having computer-executable instructions that when executed by a processor, cause performance of a method comprising:
providing a dataset having object data for an object and condition data for a condition;
processing the object data of the dataset to obtain latent object data and latent object-condition data with an object encoder;
processing the condition data of the dataset to obtain latent condition data and latent condition-object data with a condition encoder;
processing the latent object data and the latent object-condition data to obtain generated object data with an object decoder;
processing the latent condition data and latent condition-object data to obtain generated condition data with a condition decoder;
comparing the latent object-condition data to the latent condition-object data to determine a difference;
processing the latent object data and latent condition data and one of the latent object-condition data or latent condition-object data with a discriminator to obtain a discriminator value;
obtaining better latent object data, latent object-condition data or latent condition-object data, and/or latent condition data based on the discriminator value, difference between the latent object-condition data and latent condition-object data, and difference between object with generated object and condition with generated condition;
selecting a selected object based on the generated object data and latent condition-object data from a given condition; and
providing the selected object in a report with a recommendation for validation of a physical form of the object.

* * * * *